United States Patent [19]
Grosveld et al.

[11] Patent Number: 5,532,143
[45] Date of Patent: Jul. 2, 1996

[54] ISOLATED DNA MOLECULES FOR INTERGRATION SITE INDEPENDENT GENE EXPRESSION IN MAMMALIAN HOST CELLS

[75] Inventors: Franklin G. Grosveld; Dimitris Kioussis, both of London, United Kingdom

[73] Assignee: The Medical Research Council, London, United Kingdom

[21] Appl. No.: 312,498

[22] Filed: Sep. 26, 1994

Related U.S. Application Data

[63] Continuation of Ser. No. 920,536, Jul. 28, 1992, which is a continuation of Ser. No. 346,996, May 11, 1989.

[30] Foreign Application Priority Data

Aug. 7, 1987 [GB] United Kingdom .................. 8718779

[51] Int. Cl.$^6$ .............................. C12N 5/16; C12N 15/10; C12N 15/11; C12N 15/67
[52] U.S. Cl. .................. 435/69.1; 435/172.3; 435/240.2; 435/6; 536/24.1; 800/2
[58] Field of Search ............................. 536/24.1; 800/2; 435/240.2, 320.1, 69.1, 69.6, 70.1, 70.3, 70.4, 172.3

[56] References Cited

U.S. PATENT DOCUMENTS 4,663,281  5/1987  Gillies et al. ............................. 435/68

OTHER PUBLICATIONS

Thiesen et al, The EMBO Journal, vol. 5 No. 4, pp. 719–724 (1986).
Storb et al, Nature, vol. 310, 1984, pp. 238–241.
Grosveld et al, Cell, vol. 51 (Dec. 1987) pp. 975–985.
Tibtech, vol. 5 (1987) pp. 20–24.
Sewell et al, PNAS USA (Nov. 1986) vol. 83, pp. 8718–8722.
Diamond et al, PNAS USA (May 1988), vol. 85 pp. 1615–1619.
D. Tuan et al PNAS, vol. 82 (Oct. 1985) pp. 6384–6388.
G. Kollias et al. Cell, vol. 46 (Jul. 4, 1986) pp. 89–94.
M. Chao et al. Cell, vol. 32 (Feb. 1983) pp. 483–493.
G. Lang et al. The EMBO J., vol. 7 No. 6 (Jun. 1988) pp. 1675–1682.
R. Palmiter et al. Mol. Cell. Bio., vol. 13 No. 9 (Sep. 1993) pp. 5266–5275.
G. Greaver et al. Cell, vol. 56 (Mar. 24, 1989) pp. 979–986.
J. Sharpe et al. Env. J. Mol. Biol., Vol. 11 ('92) pp. 4565–4571.
D. Talbot et al. Nature, vol. 338 (Mar. 23, 1989) pp. 352–355.
A. Clark et al. Tibtech, vol. 5 (Jan. '87) pp. 20–24.
C. Pittius et al. PNAS, vol. 85 (Aug. 1988) pp. 5874–5878.
G. van Assendelft et al. Cell, vol. 56 (Mar. 24, 1989) pp. 969–977.
P. Collis et al. The EMBO J., vol. 9 No. 1 ('90) pp. 233–240.
D. Gross et al. Ann. Rev. Biochem, vol. 57 (88) pp. 159–197.
R. Mulligan Science, vol. 260 ('93) pp. 926–932.
P. Marks et al. Ann. Rev. Biochem., vol. 47 ('78) pp. 419–448.
R. Jaenisch Science, vol. 240 (10 Jun. '88) pp. 1468–1474.

Primary Examiner—Jacqueline M. Stone
Assistant Examiner—Charles Rories
Attorney, Agent, or Firm—Banner & Allegretti, Ltd.

[57] ABSTRACT

Vectors for the integration of a gene into genetic material of a mammalian host cell such that the gene may be expressed by the host cell comprise a promoter and the gene and include a dominant ectivator sequence capable of eliciting host cell-type restricted, integration site independent, copy number dependent expression of the gene.

24 Claims, 20 Drawing Sheets

FIG. 5B

3 SYNTHETIC LINKERS INSERTED
INTO AatII—PvuII FRAGMENT
OF pUC → 2.0kb VECTOR.

— GSE1364

— GSE1365

— GSE1366

ISOLATED DNA MOLECULES FOR INTERGRATION SITE INDEPENDENT GENE EXPRESSION IN MAMMALIAN HOST CELLS

This application is a continuation of application Ser. No. 07/920,536, filed Jul. 28, 1992, which is a continuation of Ser. No. 07/346,996, filed May 11, 1989.

FIELD OF THE INVENTION

The present invention relates to recombinant DNA technology and in particular to a vector useful for transfecting mammalian cells in vivo and in vitro to obtain expression of a desired structural gene. The invention relates also to the use of such sequences in gene therapy and heterologous gene expression.

BACKGROUND TO THE INVENTION

There is a continuing need for improved expression vectors exhibiting high levels of expression. In particular expression vectors for use in mammalian cell lines are of increasing importance both for the industrial production of desired polypeptides and for the development of therapies for genetic disorders.

There are many known examples of characterized structural genes, which together with appropriate control sequences may be inserted into suitable vectors and used to transform host cells. A significant problem with the integration of such a structural gene and control regions into the genome of a mammalian cell is that expression has been shown to be highly dependent upon the position of the inserted sequence in the genome. This results in a wide variation in the expression level and only very rarely in a high expression level. The problem of integration site dependence is solved by the present invention and arises from the discovery of sequences referred to herein as "dominant activator sequences" (or "dominant control regions" (DCRs)) which have the property of conferring a cell-type restricted, integration site independent, copy number dependent expression characteristic of a linked gene system.

The human β-like globin genes are a cluster of five genes in the order of 5'-ε-$^9$γ-$^A$γ-δ-β-3', comprising approximately 60 kb of DNA on the short arm of chromosome 11. The different genes are expressed in a developmentally and tissue-specific manner, i.e. the embryonic ε-gene is expressed in the yolk sac, the fetal $^9$γ- and $^A$γ-genes, primarily in the fetal liver, and the adult δ- and β-genes primarily in bone marrow (for a review, see Maniatis et al., Ann. Rev. Genet., (1981) 14, 145–178). Mutations in this gene family constitute the most widespread family of genetic diseases and a large number of these have been characterized, ranging from simple amino acid changes by point mutations to complete deletions of the locus (for a review, see Collins et al, Prog. Nucl. Acid. Res. Mol. Biol., (1984), 31, 315–462). These often lead to severe clinical problems and early death. Conventional treatment of these diseases (transfusions) are costly, risky and, in many cases, inadequate. The present invention provides a therapy for such disorders for example by gene therapy (Hock et al, Nature, (1986), 320, 275–277).

The DNA sequences which regulate the human β-globin gene are located both 5' and 3' to the translation initiation site (Wright et al., Cell, (1984), 38, 265–273; Charnay et al., Cell, (1984), 38, 251–263). Using murine erythroleukemia cells (MEL) and K562 cells at least four separate regulatory elements required for the appropriate expression of the human β-globin gene have been identified; a positively acting globin specific promoter element and a putatively negative reulatory promoter element and two downstream regulatory sequences (enhancers), one located in the gene and one approximately 800 bp downstream from the gene (Antoniou et al, EMBO J., (1988), 7(2), 377–384). A similar enhancer has also been identified downstream of the chicken β-globin gene using cultured chicken erythroid cells (Hesse et al., PNAS U.S.A., (1986), 83, 4312–4316, Choi et al, Nature, (1986), 323, 731–734). The downstream enhancer has been shown to be a developmental stage specific enhancer using transgenic mice (Kollias et al, Cell, (1986), 46, 89–94 and NAR (1987), 15, 5739–5747; Behringer et al., PNAS U.S.A. (1987), 84, 7056–7060. All of these results therefore indicate that multiple development specific control regions of the β-globin are located immediately 5', inside and 3' to the β-globin gene.

However, when a β-globin gene containing all of these control regions is introduced in transgenic mice, the gene is not expressed at the same level as the mouse β-globin gene and exhibits integration site position effects. This is characterized by a highly variable expression of the transgene that is not correlated with the copy number of the injected gene in the mouse genome. The same phenomenon has been observed in almost all the genes that have been studied in transgenic mice (Palmiter et al, Ann. Rev. Genet., (1986), 20, 465–499). Moreover, the level of expression of each injected gene in the case of β-globin is, at best, an order of magnitude below that of the endogenous mouse gene (Magram et al., Nature, (1985), 315, 338–340; Townes et al., EMBO J., (1985), 4 1715–1723; Kollias et al, Cell, (1986), 46, 89–94). A similar problem is observed when the β-globin or other genes are introduced into cultured cells by transfection or retroviral infection. This poses a big problem when considering gene therapy by gene addition in stem cells. It is also a major problem for the expression of recombinant DNA products from tissue cells. Extensive screening for highly producing clones is necessary to identify cell-lines in which the vector is optimally expressed and selection for vector amplification is generally required to achieve expression levels comparable to those of the naturally occurring genes, such as for example β-globin genes in erythroleukemic cell-lines.

The study of the β-globin system has been assisted by analysis of hemoglobinpathies such as thalassemias (van der Ploeg et al, Nature, (1980), 283, 637–642; Curtin et al, In: Haemoglobin Switching: Fifth Conference on Haemoglobin Switching, Washington Ed. G. Stamatoyannopoulos, Alan R. Liss Inc., New York 1987). The Dutch thalassemia is heterozygous for a large deletion which removes 100 kb upstream of the β-globin gene, but leaves the β-globin gene, including all of the control regions described above intact (Kioussis et al, Nature, (1983), 306, 662–666; Wright et al Cell, (1984), 38, 265–273; Taramelli et al, NAR, (1986), 14 7017–7029). Since the patient is heterozygous and transcribes the normal locus in the same nucleus, it indicates that some control mechanism may be overriding the functioning of the control sequences immediately surrounding the genes in the mutant locus. In the case of the Dutch γβ-thalassemia there are two possible explanations the observed effects; either a cis acting positive element has been removed or there has been insertion of a negative-acting element in an inactive chromatic configuration and behaves like a classical position effect (Kioussis et al, Nature, (1983), 306, 662–666).

In a chromosome, the genetic material is packaged into a DNA/protein complex called chromatin which has the effect of limiting the availability of DNA for functional purposes. It has been established that many gene systems (including the β-globin system) possess so-called DNase hypersensitive sites. Such sites represent putative regulatory regions, where the normal chromatin structure is altered to allow interaction with trans-acting regulatory regions.

Regions upstream from the epsilon-globin gene and downstream from the β-globin gene which contain a number of "super" hypersensitive sites have been identified. These sites are more sensitive to DNase I digestion in nuclei than the sites found in and around the individual genes when they are expressed (Tuan et al PNAS U.S.A., (1985), 32, 6384–6388; Groudine et al, PNAS U.S.A., (1983), 80, 7551–7555. In addition, they are erythroid cell specific and they are present when any one of the globin genes is expressed.

Tuan et al describe the broad mapping of four major DNase I hypersensitive sites in the 5' boundary area of the "β-like" globin gene. The authors note that certain sequence features of these sites are also found in many transcriptional enhancers and suggest that the sites might also possess enhancer functions and be recognized by erythroid specific cellular factors.

The present invention arose from the discovery that the complete β-globin locus with intact 5' and 3' boundary regions does not exhibit an integration site position dependence. The regions of the locus responsible for this significant characteristic have been determined and shown to correspond to the DNase I super hypersensitive sites. These dominant activator regions are quire distinct from enhancers, exhibiting properties such as integration site independence not exhibited by the known enhancers. The dominant activator sequence used in conjunction with the known promoter/enhancer elements reconstitute full expression of the natural gene. The connection made as part of the present invention between DNase I super hypersensitive sites and dominant activator regions allows the invention to be extended to gene systems other than the β-globin gene system. It has been shown, for example, that a human β-globin gene can be functionally expressed in transgenic mice in an integration site independent manner. Human T-lymphocytes (T-cells) are produced in bone marrow and mature in the thymus where they develop their immunological characteristic of responding to foreign antigens in the body. T-cells are produced in a highly tissue specific manner. It is recognised that T-cells carry specific cellular markers (Bernard et al "Leukocyte Typing", Ed. Bernard et al, p41, Springer Verlag, Berlin and New York, 1984). One such marker is the E-rosette receptor, known by the designation CD2. The structure of the CD2 marker and the CD2 genes has been the subject of considerable study (Brown et al, Meth. in Enzym., (1987), 150, 536–547 and Lang, G. et al, EMBO J, (1988), 7(6), 1675–1682).

In the latter paper, published after the priority date of the present invention, the property of a large fragment including the CD2 gene to exhibit copy number dependence is noted and a suggestion is made that such a fragment contains a locus forming sequence analogous to those found in β-globin. DNase super hypersensitive sites have now been identified in the fragment and shown to be dominant activator sequences of the present invention.

Finally, the present invention is applicable to the production of transgenic animals and the techniques for producing such are now widely known. For a review, see Jaenisch, Science, (1988), 240, 1468–1474.

The present invention provides a solution to the problem of integration site dependence of expression making possible the insertion of functionally active gene systems into mammalian genomes both in vitro and in vivo. Specific sequences providing advantageous increases in transcription levels have also been identified.

SUMMARY OF THE INVENTION

According to the present invention there is provided a vector for the integration of a gene into the genetic material of a mammalian host cell such that the gene may be expressed by the host cell, the vector comprising a promoter and the gene characterised in that the vector includes a dominant activator sequence capable of eliciting host cell-type restricted, integration site independent, copy number dependent expression of the gene.

As used herein the term "dominant activator sequence" means a sequence of DNA capable of conferring upon a linked gene expression system the property of host cell-type restricted, integration site independent, copy number dependent expression when integrated into the genome of a host cell compatible with the dominant activator sequence. Such a dominant activator sequence retains this property when fully reconstituted within the chromosome of the host cell. The ability to direct efficient host cell-type restricted expression is retained even when fully reformed in a heterologous background such as a different part of the homologous chromosome (e.g. chromosome 11 for β-globin) or indeed a different chromosome altogether.

It is hypothesized that the dominant activator sequences of the invention may open the chromatin structure of the DNA, making it more accessible and thus may act as a locus organizer. The dominant activator sequence may be a single contiguous sequence corresponding to, or derived from a naturally occurring gene system or may consist of two or more such sequences linked together with or without intervening polynucleotides.

The dominant activator sequence may be derived by recombinant DNA techniques from a naturally occurring gene system or may correspond to a naturally ocurring gene system in the sense of being manufactured using known techniques of polynucleotide synthesis from sequence data relating to a naturally occurring gene system. Alterations of the sequence may be made which do not alter the function of the dominant activator sequence.

Preferably, the naturally occurring gene system from which the dominant activator sequence is derived or with which it corresponds is a system which exhibits a highly host cell-type restricted expression characteristic preferably at a high level. Specific examples of such systems are the hemoglobin systems such as β-globin system and lymphocyte systems such as the CD2 system.

The dominant activator sequence may consist of, be derived from, or correspond to one or more DNase I super hypersensitive site, preferably of any gene system capable of cell specific expression. Other sequences might however exhibit the functional characteristics of a dominant activator sequence. Where the naturally occurring dominant activator sequence comprises two or more subsequences separated by an intervening polynucleotide sequence or sequences the dominant activator sequence may comprise two or more of the subsequences linked in the absence of all or a part of one or more of the intervening sequences. Thus, if the dominant activator sequence of a naturally occurring gene locus comprises two or more discrete subsequences separated by intervening non functional sequences, (for example, two or more super hypersensitive sites) the vector of the invention may comprise a dominant activator sequence comprising two or more of the subsequences linked together with all or part of the intervening sequences removed.

The term "vector" as used herein connotes in its broadest sense any recombinant DNA material capable of transferring DNA from one cell to another.

The vector may be a single piece of DNA in linear or circular form and may, in addition to the essential functional elements of the invention, include such other sequences as are necessary for particular applications. For example, the vector may contain additional features such as a selectable marker gene or genes, and/or features which assist translation or other aspects of the production of a cloned product. The vector suitable for integration consists of an isolated DNA sequence comprising a dominant activator sequence and an independent structural gene expression system.

The DNA sequence is not linked at either end to other substantial DNA sequences. The isolated DNA sequence may however be provided with linkers for ligation into a vector for replication purposes or may be provided with sequences at one or both ends to assist integration into a genome.

The vector defines a "mini locus" which can be integrated into a mammalian host cell, where it is capable of reconstructing itself in a host cell-type restricted, integration site independent, copy number dependent manner.

The invention also provides a transfer vector, suitably in the form of a plasmid, comprising a dominant activator sequence. Such vectors are useful in the construction of vector for integration.

The term "gene" as used herein connotes a DNA sequence, preferably a structural gene encoding a polypeptide. The polypeptide may be a commercially useful polypeptide, such as a pharmaceutical and may be entirely heterologous to the host cell. Alternatively the gene may encode a polypeptide which is deficient absent or mutated in the host cell.

The mammalian host cell may be any mammalian host cell susceptible to uptake of the vector of the invention. The vector DNA may be transferred to the mammalian host cell by transfection, infection, microinjection, cell fusion, or protoplast fusion. The host cell may be a cell of a living human or animal. In particular, the host cell may be a cell of a transgenic animal such as a mouse. The host cell may be a human stem cell such as bone marrow cell. The host cell may be derived from tissue in which the dominant activator sequence is functional, such as erythroid cells in the case of the β-globin locus.

The promoter may be any promoter capable of functioning in the host cell and may be for example a mammalian or viral promoter. Optionally, the promoter may be homologous with the gene locus of the dominant activator sequence (for example the β-globin promoter) and may be present in tandem with another promoter (for example the β-globin promoter) and a viral tk or SV40 promoter and may include one or more enhancer elements.

In one embodiment of the invention to be described below, the dominant activator sequence is derived from the β-globin gene locus. As discussed above, the β-globin locus contains a number of DNase I super hypersensitive sites which constitute the dominant activator regions (see Tuan et al loc cit). Preferably the dominant activator sequence contains one or more of the DNase I super hypersensitive sites identified within the β-globin locus. Preferably these are from the 5' boundary of the locus, optionally with the 3' boundary sequences. The dominant activator sequence is within a fragment of 21 kb from −1 kb ClaI to −22 kb BglII immediately upstream of the epsilon-globin gene in the β-globin locus. This region contains four DNase I super hypersensitive sites with intervening polynucleotides (five distinct sites of which two are very close together). Preferably some or all the intervening nucleotides are removed using known techniques such as digestion with exonuclease.

A reduced form of the β-globin locus dominant activator sequence has been produced which exhibits a significantly increased level of expression of a linked gene expression system. This was produced by ligating the following four fragments 2.1 kb XbaI—XbaI 1.9 kb HindIII—HindIII 1.5 kb KpnI-BglII 1.1 kb partial SacI fragment This dominant activator sequence, referred to herein as a "micro locus" is a 6.5 kb fragment which may be used as a "cassette" to activate a specific gene expression system.

In a second embodiment of the invention to be described below, the dominant activator sequence is derived from the CD2 gene locus. The CD2 gene locus contains three super hypersensitive sites, one at the 5' boundary of the locus and two at the 3' boundary of the locus. Preferably the dominant activator contains one or more of the DNase I super hypersensitive sites within the CD2 locus. Most preferably, the dominant activator sequence contains both the super hypersensitive sites from the 3' boundary of the locus, optionally with all or a part of any intervening sequence deleted. The dominant activator sequence is contained within a 5.5 kb BamHI to XbaI fragment 3' to the CD2 gene. In a further aspect of the invention there is provided a method of producing a polypeptide comprising culturing a host cell transformed with a vector of the invention.

The method may be applied in vitro to produce a desired polypeptide. In addition, the method may be applied in vivo to produce a polypeptide having no therapeutic value to the animal. Such a method of producing a polypeptide is not to be considered as a method of treating the human or animal body.

In a further aspect of the invention the vector may be used in a method of treatment of the human or animal body by replacing or supplementing a defective mammalian gene.

Many diseases of the human or animal body result from deficiencies in the production of certain gene products. The characterizing features of the vectors of this invention make them amply suited to the treatment of deficiencies by gene therapy in vivo.

A method of gene therapy is provided comprising removing stem cells from the body of a human or an animal, killing stem cells remaining in the body, transforming the removed stem cells with a vector of the invention containing a gene deficient, or absent, in the human or animal body, and replacing the transformed stem cells in the human or animal body. This method can be used to replace or supplement a gene deficient in a human or animal. For example, an individual suffering from a hemoglobinopathy such as β-thalassemia could be treated to insert an active highly expressed β-globin gene locus to make up the deficient β-haemoglobin. Alternatively a deficiency in the immune system could be treated with a CD2 locus vector. This method could be used to treat deficiencies in adenosine deaminase (ADA syndrome) or severe combined immune deficiency syndrome (SCID syndrome).

Bone marrow is a suitable source of stem cells and is advantageous in that it contains the precursors of both lymphocytes and erythroid cells. Alternatively other tissue could be removed from the body, transfected or otherwise provided with a vector of the invention and implanted back into the body.

The invention is now described by way of example with reference to the accompanying drawings.

BRIEF DESCRIPTION OF THE DRAWINGS

FIGS. 5A–D shows an expression analysis of the human β-globin transgene in mouse (FIG. 5 comprises 5A, 5B, 5C, 5D).

EXAMPLE 1

Experiments were conducted to establish whether dominant control regions are present in the flanking regions of the β-globin locus by including such regions in a β-globin construct. If such sequences were insensitive to the integration site position effects, it would be expected: (1) that the level of expression of the construct is directly related to its copy number in the transgenic mice, (2) that the level of expression per gene copy is the same in each mouse and (3) possibly that the introduced gene is expressed at a level comparable to that of the mouse genes. Prior to testing the 5' and 3' sequences, it was important to carefully map the positions of the hypersensitive sites since their exact position, especially at the 3' side, has not been published in detail (Tuan et al., 1985).

Mapping DNase Hypersensitive Sites Flanking the β-globin Locus

Figure 1:
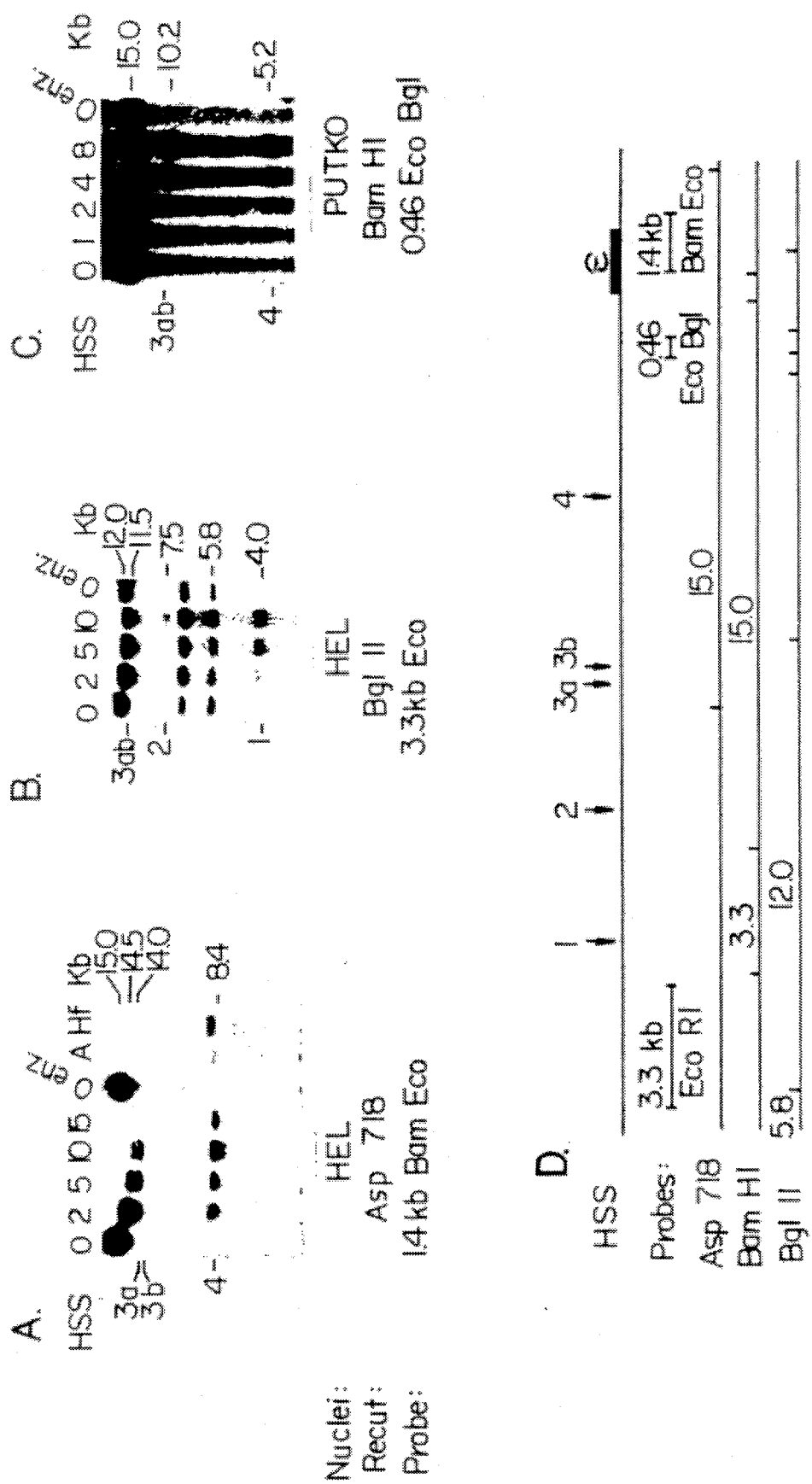
FIG. 1(A–D) shows the mapping of DNase I super hypersensitive sites 5' to the epsilon globin gene. Panels A to C are representations of nitrocellulose filters illustrating the mapping experiment and Panel D shows a restriction map of the β-globin locus upstream of the epsilon globin gene for the three restriction enzymes used in these experiments. Probe locations and super hypersensitive sites are marked.

Very limited DNaseI digestion of nuclei of erythoid cells reveals sites extremely sensitive to DNase upstream of the epsilon-globin gene and downstream of the β-globin gene (Tuan et al., 1985). We fine mapped the DNaseI hypersensitive sites relative to restriction sites mapped in our cosmids (Taramelli et al., 1986). FIG. 1 shows a time course of DNaseI digestion on nuclei of HEL (Martin and Papayannopoulou, 1982) and PUTKO (Klein et al., 1980) cells recut with various restriction enzymes, Southern blotted and hybridized with a number of probes upstream of the epsilon-globin gene (FIG. 1d). Four hypersensitive sites are present at 18 kb (No. 1), 15 kb (No. 2), 12.0 and 11.5 kb (No. 3a,b) and 5.4 kb (No. 4) upstream of the epsilon-globin gene. Nos. 1, 3a and 4 sites are strong hypersensitive sites as judged by their early appearance during the time course of digestion. Nos. 2 and 3b sites are weaker sites and appear later during digestion. In FIG. 1, the experimental details were as follows:

Panel A

Nuclei of HEL cells were incubated with DNase (60 μg/ml) at 37° C. and aliquots removed from the reaction at the times indicated (in minutes) above each track.

Aliquots of approximately $10^7$ HEL nuclei were incubated in the absence of DNaseI (0 enz.) or presence of 30 units of AluI or 60 units of HinfI for 15 min. at 37° C. DNA was purified after proteinase K digestion, recut with Asp718, fractioned on a 0.6% agarose gel transferred to nitrocellulose and probed with an epsilon-globin gene probe (Bam-Eco 1.4 kb).

Panel B

The DNaseI digested samples of Panel A were recut with BglII and probed with a 3.3 kb EcoRI fragment which in addition to 12.0 and 5.8 kb bands also detects a cross hybridizing band of 6.8 kb after washing filters at a stringency of 0.3×SSC 65° C., which is not observed on washing at 0.1×SSC 65° C. (not shown).

Panel C

Nuclei of PUTKO cells were digested with DNaseI (20 μg/ml) at 37° C. and samples removed from the reaction after 1, 2, 4 and 8 minutes. An aliquot of approximately $10^7$ nuclei was incubated for 8 minutes at 37° C. in the absence of DNaseI (lane 0 enz.). After recutting with BamHI gel electrophoresis and transfer to nitrocellulose, the filter was hybridized with a 0.46 kb EcoRI-BglII probe and washed to a final stringency of 0.3×SSC at 65° C.

Panel D

Shows a restriction map of the β-globin locus upstream of the epsilon-globin gene for the three restriction enzymes used in these experiments. Locations of probes and deduced positions of DNaseI hypersensitive sites in HEL and PUTKO chromatin are marked.

Figure 2:
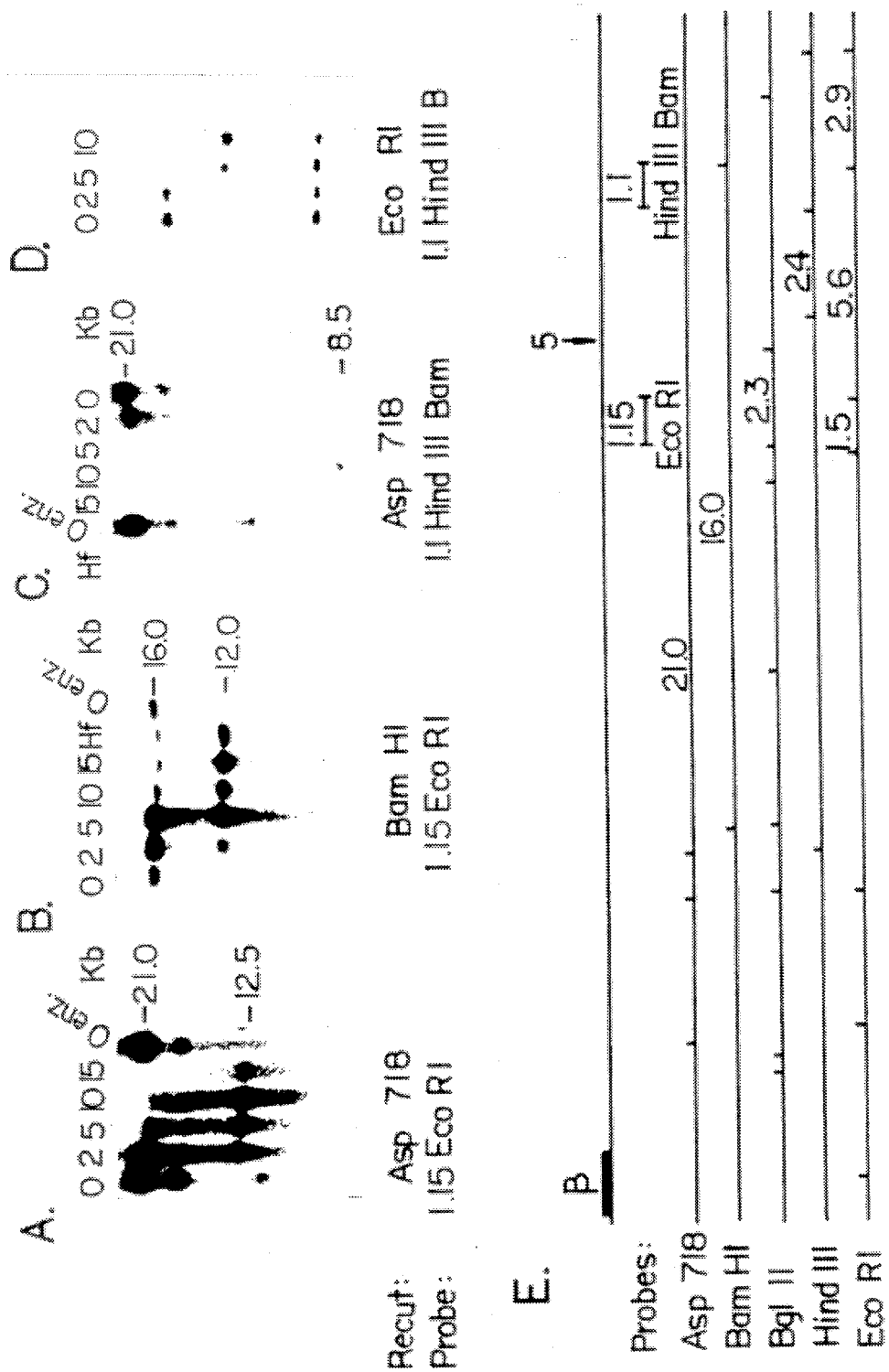
FIG. 2 (A–E) shows the corresponding experiment to that in FIG. 1 conducted to map the super hypersensitive sites 3' of the β-globin gene.

The exact location of the DNaseI hypersensitive site 3' of the adult β-globin gene was determined using two single copy DNA probes and several restriction enzyme digests of DNaseI digested HEL nuclei. The data summarised in FIG. 2 (A–D) show that there is a single DNaseI hypersensitive site between the 2.3 kb BglII fragment and the 2.4 kb HindIII fragment approximately 20 kb 3' of the adult β-globin gene (FIG. 2E). (Similar results were obtained with DNaseI digested PUTKO nuclei (data not shown).

In FIG. 2 the experimental details were as follows:

Panels A to D show DNA from DNaseI digested nuclei of HEL cells recut with the indicated restriction enzymes and probed with either a 1.15 kb EcoRI or a 1.1 kb HindIII-Bam fragment. Both DNA probes contain some human repetitive DNA which necessitated the use of 10 μg sheared human DNA per ml in prehybridization and hybridization buffers. Filters were washed to a final stringency of 0.3×SSC at 65° C.

Panel E shows a restriction map of the β-globin locus 3' of the β-globin gene. The position of the two probes used and the 3' HSS site are marked. The position of HSS 5 was confirmed by probing HindIII and BglII recut DNA samples with the 1.15 EcoRI probe (data not shown).

Construction of the β-globin "Mini" Locus

The globin "mini" locus (FIG. 3) was constructed from three regions (see "Materials and Methods" below for the precise description); a 21 kb region immediately upstream of the epsilon-globin gene (−1 kb ClaI to −22 kb BglII) containing all four hypersensitive sites (FIG. 1), a 4.7 kb (BglII) fragment containing the β-globin gene and all the known regulatory sequences immediately in and around the gene and a 12 kb region downstream from the β-globin gene (+12 kb KpnI to +24 kb BamHI) containing the downstream hypersensitive site (FIG. 2). These regions contained or were provided with unique linkers to create a series of unique restriction sites (SalI, XhoI, ClaI, KmnI, PvuI) and cloned into the cosmid pTCF (Grosveld et al., 1982). The entire 38 kb insert was excised from the cosmid as a SalI fragment, purified from low melting agarose and injected into fertilized mouse eggs (Kollias et al., 1986).

Figure 3:
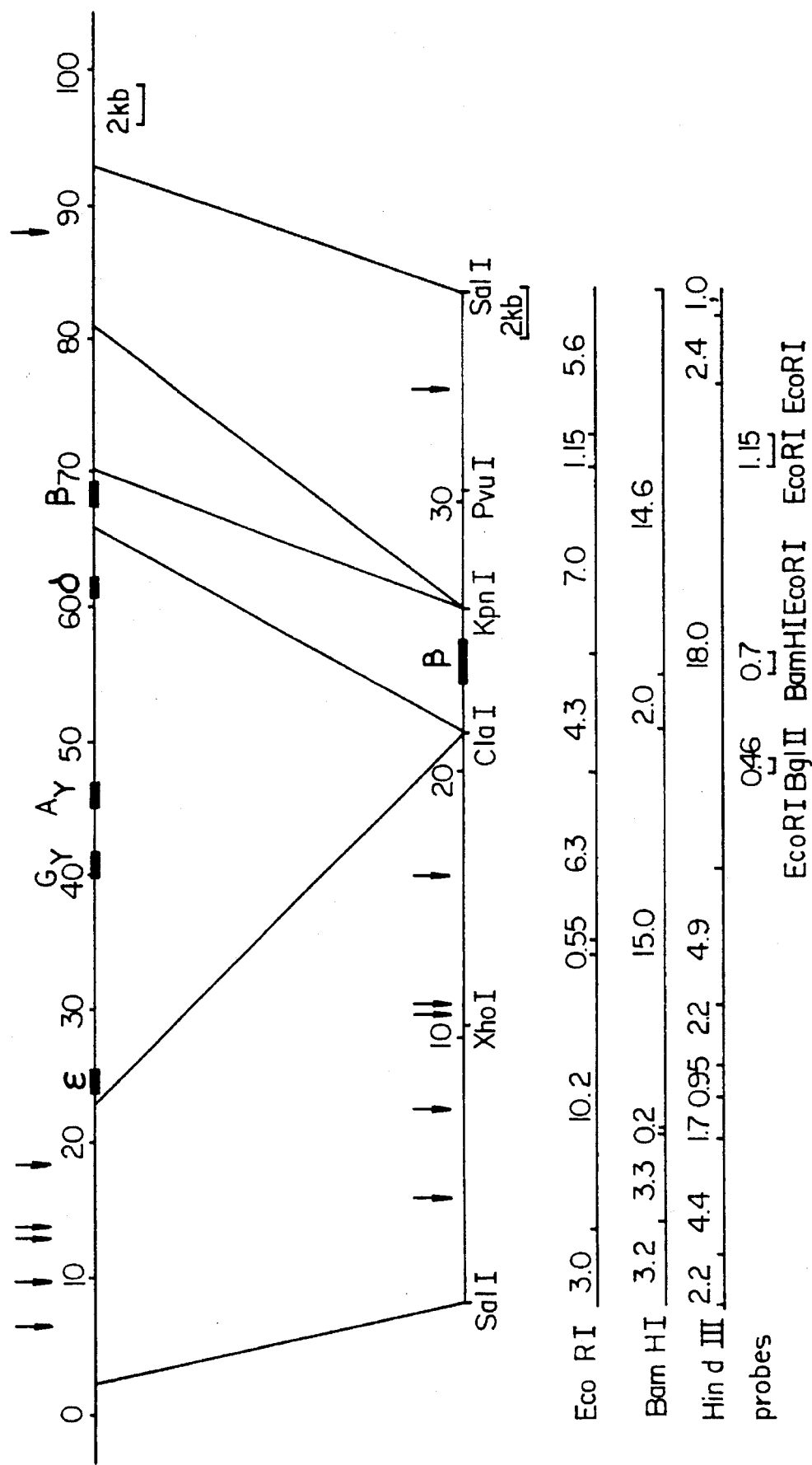
FIG. 3 shows the construction of a human β-globin "mini" locus.

Referring to FIG. 3, the human β-globin locus is illustrated on top and the sizes are shown in kilobases (kb). The second line shows the β-globin "mini" locus, with a number of unique restriction sites; the connecting lines indicate the original position of the fragments in the β-globin locus. The restriction enzyme fragments in the "mini" locus for EcoRI, BamHI and HindIII are shown in kb. The hybridization probes for the 5' flanking region (EcoBgl 0.46), the β-globin gene (BamEco 0.7 IVS II) and the 3' flanking region (Eco 1.15) are shown at the bottom.

Transgenic Mice Containing the β-globin "Mini" Locus

Figure 4A:
FIGS. 4A–C shows a structural analysis of the human β-globin transgene (FIG. 4 comprises 4A, 4B, 4C).
Figure 4B:
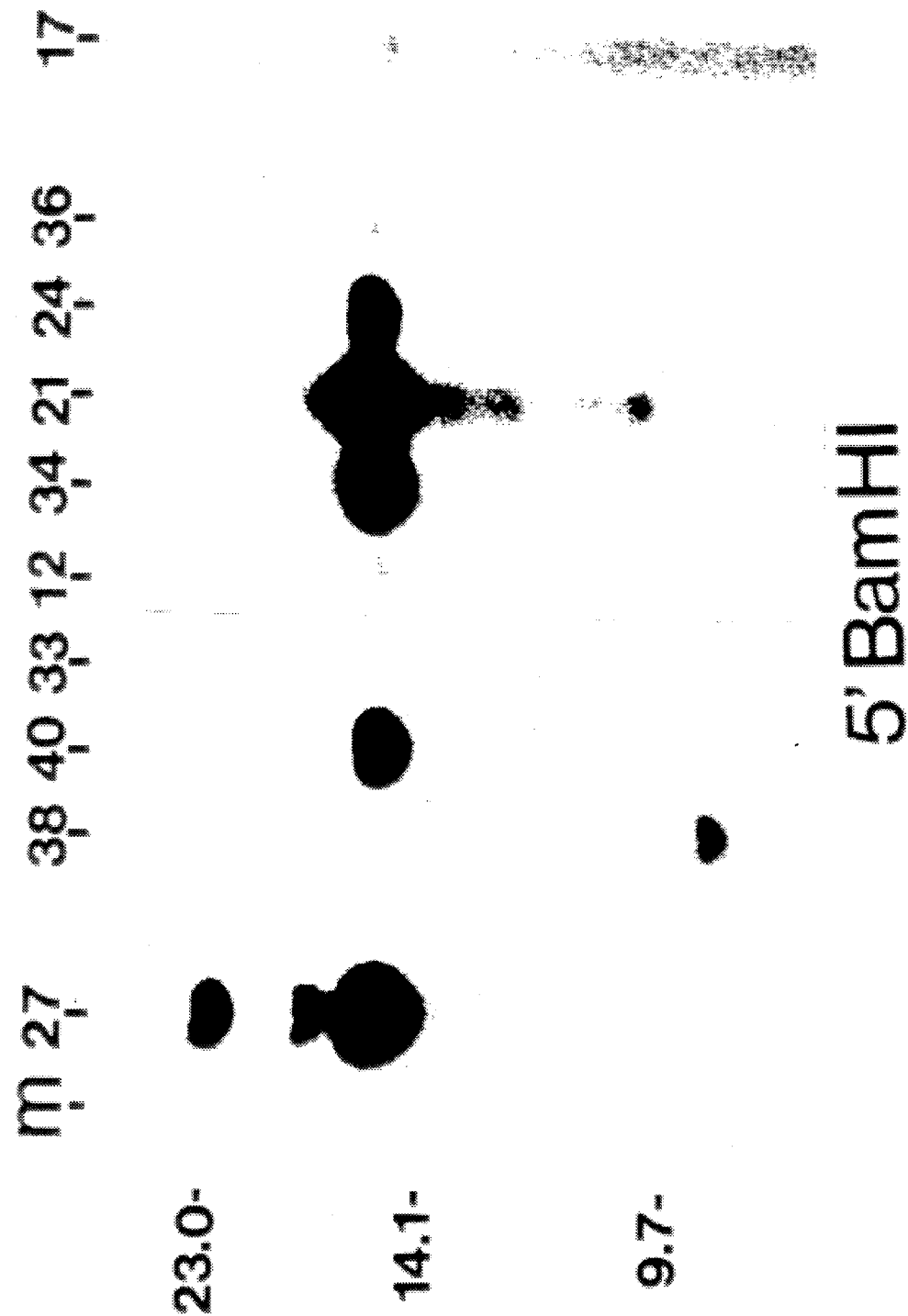
Figure 4C:

Initial injection of mouse eggs was carried out with a DNA concentration of 2 μg/ml, the eggs were transplanted back into the mice, but no offspring were obtained (for unknown reasons). Several series of injections were then carried out with a DNA concentration of 0.5–1 μg/ml and fetuses were collected after either 12.5 or 13.5 days of gestation. DNA was prepared from individual placentas, Southern blotted and hybridized with a human β-globin probe to determine the number of transgenic mice (as described by Kollias et al., 1986). The transgenic DNAS were subsequently digested with EcoRI, Southern blotted and hybridized with a human β-globin probe and a mouse Thy-1 probe (single copy) to determine the number of genes integrated in each mouse (FIG. 4A and Table I—see page 29). These values varied from a single insert (mouse 33 and 38) up to a hundred copies per cell (mouse 21). It was then determined whether the inserted DNA was integrated intact or whether deletions and/or rearrangements had taken place after injection. Total DNA was digested with BamHI or HindIII, Southern blotted and probed for the presence of the complete construct. In particular a 0.46 kb BglII probe (FIG. 3) was used to detect the 15 kb BamHI fragment at the 5' end of the construct (FIG. 4B) and a 1.15 kb EcoRI probe (FIG. 3) to detect the 14.6 kb BamHI or 18 kb HindIII fragment at the 3' end of the construct (FIG. 4C). All but one of the transgenic mice appeared to have intact "mini" β-globin loci which are integrated in tandem arrays (not shown) as judged by the presence of the correctly sized fragments. It should be noted however that the BamHI and HindIII sites at the 3' end of the locus (FIGS. 4 and 6) are very resistant to cleavage, even though the mixed-in control DNA has been fully digested (see Methods). This results in partial cleavage bands which are larger than fully digested BamHI (14.6 kb) and HindIII (18 kb) fragments. Transgenic mouse 38 is the only mouse that has not retained a full copy of the β-globin "mini" locus. The single copy present in this mouse has lost the BamHI and HindIII sites upstream of the β-globin gene, although the EcoRI site is still present. This indicates that all the 5' flanking DNA including the whole hypersensitive site region has been deleted in this mouse.

In FIG. 4, the experimental details were as follows:

Panel A

Approximately 5 μg of placental or yolk sac DNA was digested with EcoRI, Southern blotted after gel electrophoresis and hybridized to either the human β-globin Bam-Eco IVS II probe or a mouse Thy-1 probe. The gels were quantitated by densitometer scanning of different exposures. The DNA of mouse 17 was partially degraded, therefore, a lower M.W. Thy-1 cross hybridizing band was used to quantitate this sample. The insert (a high exposure of the globin hybridization) shows the low copy signals.

Panel B

Placental or yolk sac DNA was digested with BamHI, Southern blotted and hybridized to a 5' flanking probe (Eco-Bgl 0.46, FIG. 3).

Panel C

Placental or yolk sac DNA was digested with BamHI or HindIII, Southern blotted and hybridized to a 3' flanking probe (Eco 1.15, FIG. 3).

In all panels a mixture of marker DNA was used from a DNA digested with BstEII or HindIII. The transgenic mice are indicated at the top, empty lanes contain DNA samples from non-transgenic mice. Sizes are in kilobases (kb). Some of the DNA samples are partially digested, although the mixed-in DNA control was completely digested (not shown). This result in bands which are larger than the 14.6 kb BamHI (14.6 kb+3.2 kb +3.3 kb) or the 18 kb HindIII fragments (18 kb+2.4 kb+3.4 kb) by cleavage at the next BamHI or HindIII site in the tandem arrays.

The Human β-globin "Mini" Locus is Fully Active

Figure 5A:
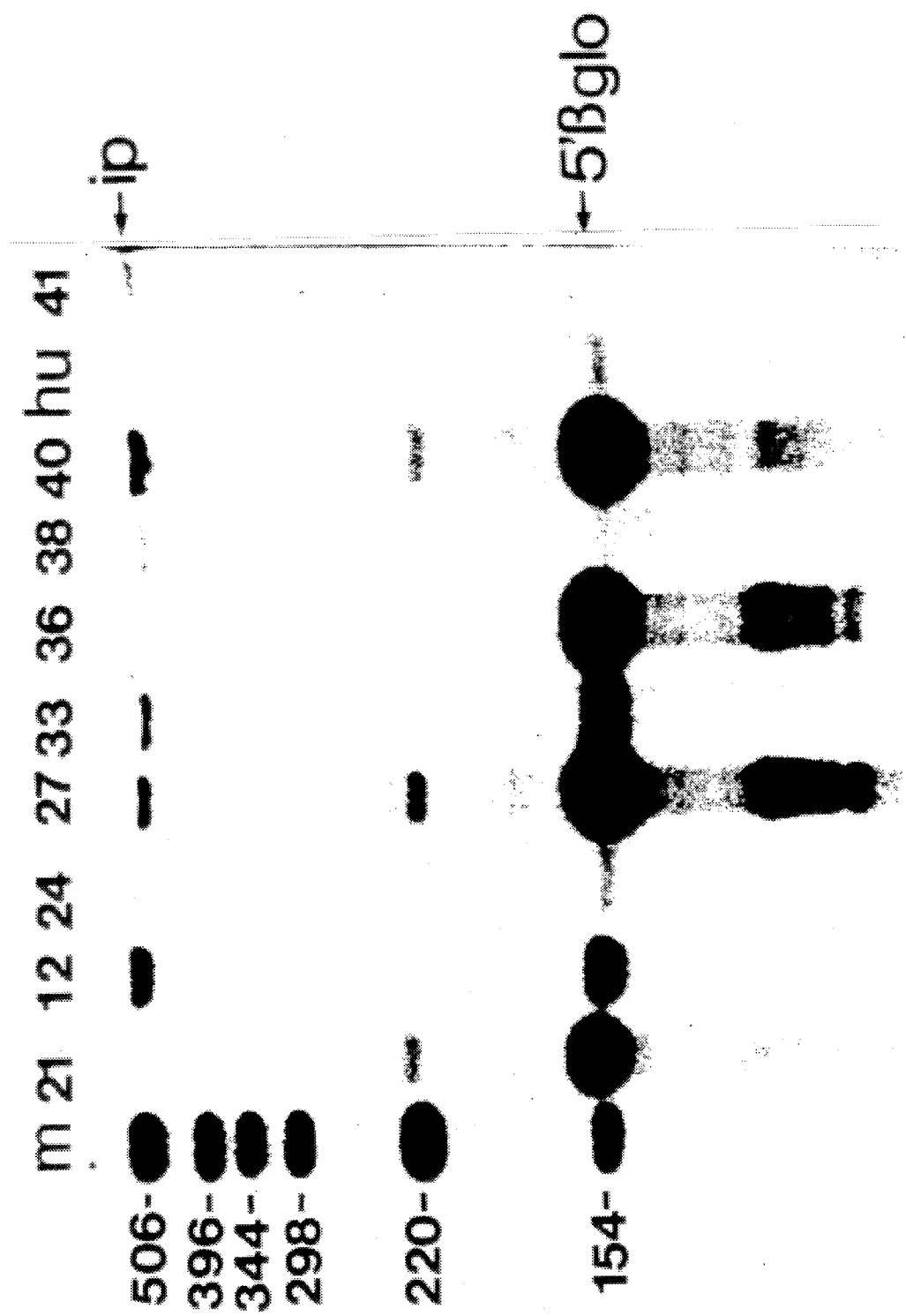
Figure 5B:
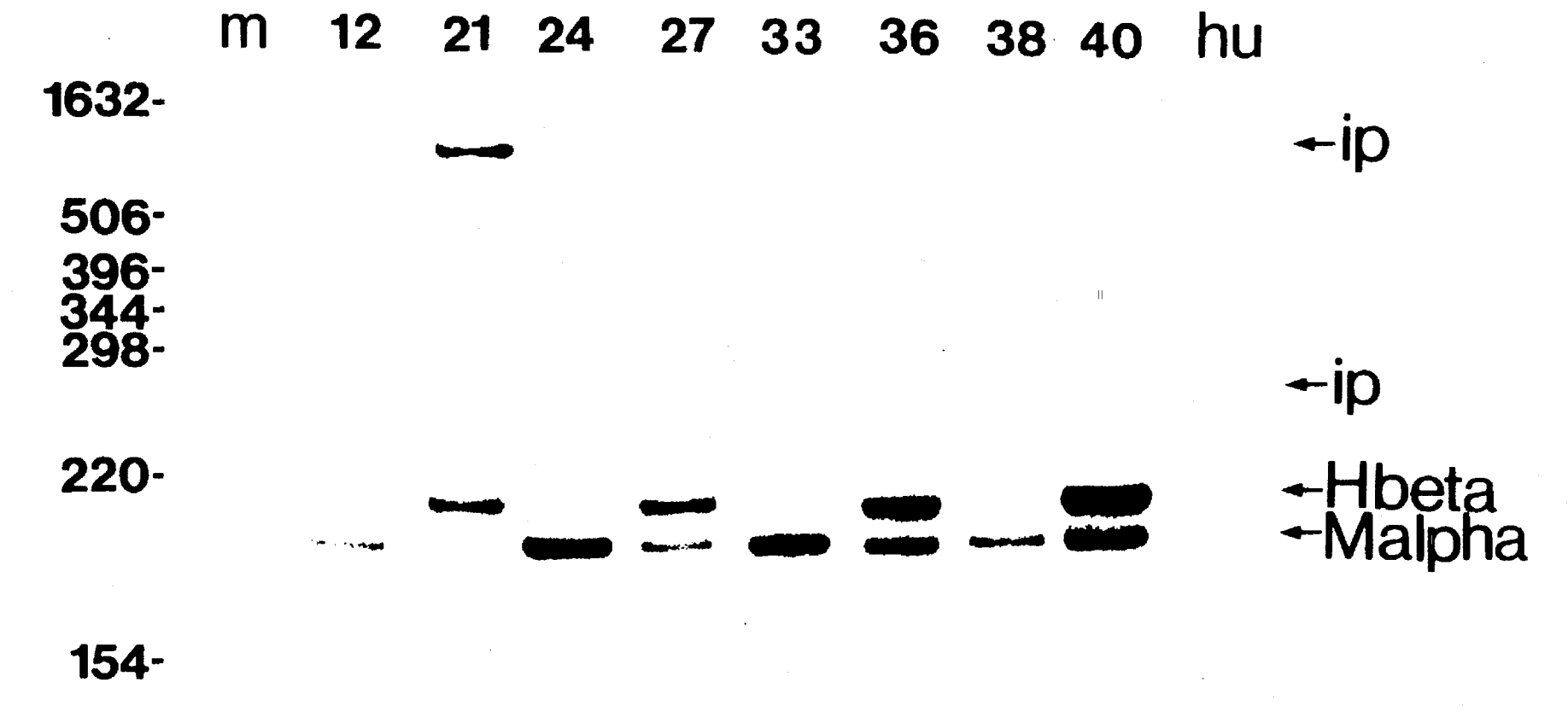
Figure 5C:
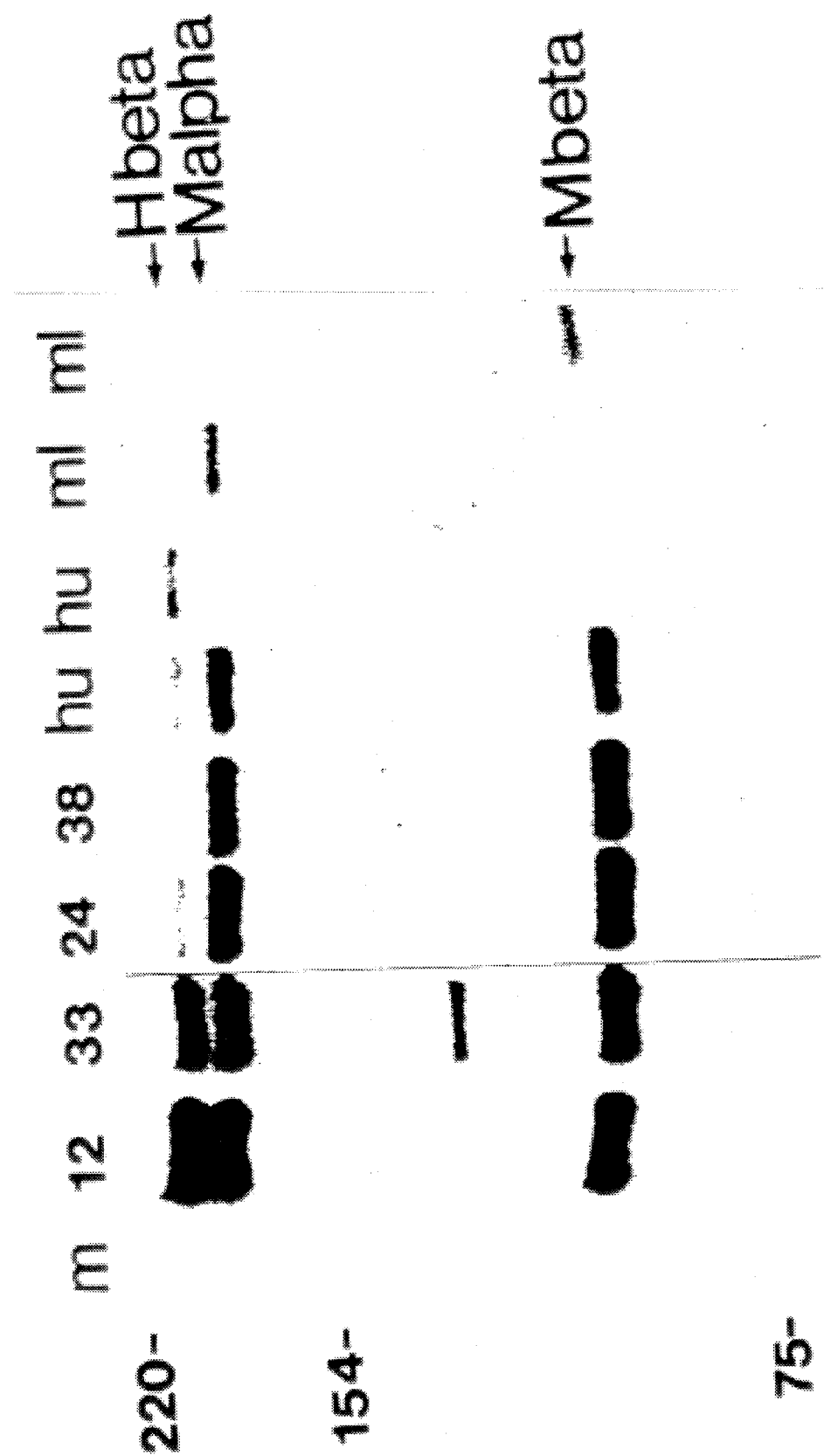
Figure 5D:
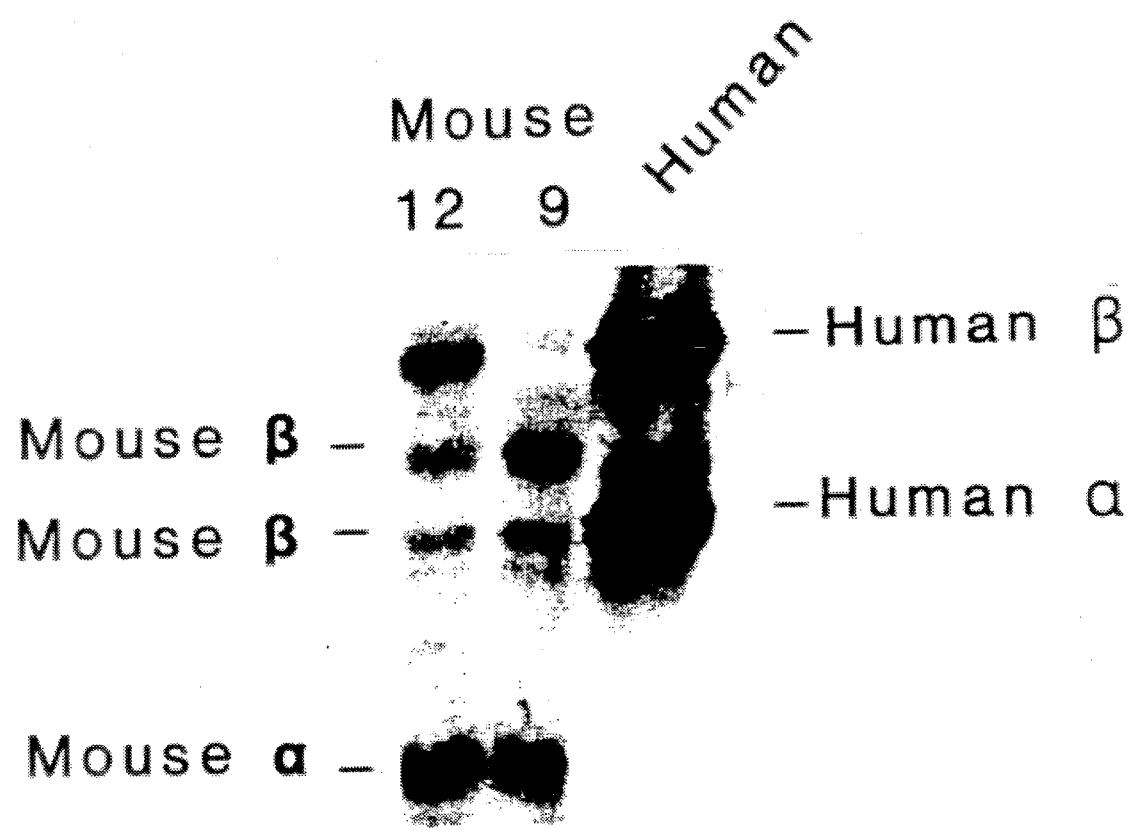

To measure the activity of the human β-globin gene, RNA was prepared from all the transgenic and non-transgenic mice (liver, blood and brain) and analyzed by S1 nuclease protection analysis. FIG. 5A shows the analysis of liver RNA with a 5' human β-globin, while FIG. 5B shows an analysis of the 3' end of the human β-globin RNA in the presence of a 3' mouse β-globin and mouse α-globin probes as internal controls. These results show that the human β-globin gene is correctly initiated and polyadenylated and that the levels of RNA are proportional to the number of copies of the "mini" locus in each mouse, (except 24 and 38, see below). Moreover, no expression is found in non-erythroid tissue (not shown). The level of expression is clearly very high when the ratio of the human β- to mouse β-globin RNA levels (Table I see page 29) is compared to that of the Hu11 cells control (Zavodny et al., 1983). The latter cell line is a mouse erythroleukemia (MEL) cell line containing the human β-globin locus on a human X-11 hybrid chromosome. To carefully quantitate the levels of expression in these mice, RNA levels in mice 33 and 12 which have one and two intact copies of the β-globin locus were analyzed, and the two exceptions mice 24 and 38 with mouse and human β-globin probes of equal specific activity. FIG. 5C shows that the signal of the human β-globin gene is approximately half that of the mouse β-globin diploid in mouse 33 and equal in mouse 12. This is confirmed at the protein level when the red cells of mouse 12 and an age-matched control are lysed and the proteins run on a Triton-acid urea gel (Alter et al., 1980). It is clear that the trangenic mouse 12 expresses equal levels of mouse and human β-globin proteins (FIG. 5D). From all these data it was concluded that each human β-globin gene in these mice is fully active, i.e. at a level equivalent to that of the mouse β-globin genes, while the expression in mice 24 and 38 is suppressed. A peculiar situation is found in mice 21 and 17. The mouse β-globin RNA levels are very low in these mice, presumably as a result of the very high copy number of the human β-globin gene and, as a consequence, very high mRNA (and protein) levels. The high copy number possibly results in a competition for transcription factors (mouse β-globin RNA is decreased more that mouse α-globin RNA, FIG. 5B), while the high levels of β-globin protein definitely result in an anemia (α-thalassemia). Mice 21 and 17 had small colourless livers consistent with the destruction of mature red cells and a concomitant loss of mRNA.

Figure 6:
FIG. 6 shows the production of human β-globin DNA in various mouse tissues (ys=yolk sac, lv=Foetal liver and br=brain).
Figure 6:

Two mice (38 and 24) form an exception because they express relatively lower amounts of human β-globin (FIG. 5A,B,C, Table 1 see page 29). The situation in mouse 38 is explained by the fact that this is the only transgenic mouse which has a deletion of the 5' end of the locus (FIG. 4). As a consequence, the human β-globin gene is still expressed, but in a position dependent manner and at low levels, just as found when small β-globin fragments are introduced in mice (Kollias et al., 1986; Magram et al., 1985; Townes et al., 1985). Mouse 24 has no apparent defect in the locus and the possibility was investigated that this mouse is a true exception or whether it is either a chimeric mouse or has the β-globin locus integrated on an inactive X-chromosome. DNA was therefore isolated from the yolk sac, brain and fetal liver (the "erythroid" tissue) and hybridized the EcoRI digested DNAs on Southern blots with a human β-globin probe and a murine Thy-1 probe to detect the β-globin transgene versus an endogenous single copy gene. FIG. 6 clearly shows that 10 µg of fetal liver DNA contains even less than half of the globin signal that 5 µg of yolk sac DNA, i.e. much less than 25% of the liver cells contain the β-globin gene. This is therefore a chimeric mouse, in which the β-globin mini locus is under-represented in the erythroid tissue (fetal liver) which explains the lower levels of human β-globin mRNA found in these cells. It may be concluded from this that provided the locus has not been affected, there is a complete correlation between expression levels and DNA copy numbers and that each gene is fully expressed in every transgenic mouse. In FIG. 5, the experimental details were as follows:

Panel A

5 µg of RNA from 12.5 or 13.5 day livers from different mice (numbers on top) was analyzed by S1 nuclease protection as described previously (Kollias et al., 1986). The protected fragment of the 5' human β-globin probe (525 bp AccI from an IVS I lacking β-globin gene) is 160 nt (5' βglo). Input probe is shown as ip. The marker (m) is pBR322 DNA digested with HinfI and the sizes are indicated in nucleotides.

Panel B

5 µg of RNA was analyzed as in panel A, but using two probes; a 3' probe of the human β-globin gene (760 bp EcoRI-MspI) resulting in a 210 nt protected fragment (H beta) and a mouse α-globin probe (260 bp BamHI second exon probe), resulting in a 170 nt protected fragment (M alpha). The positive control is RNA from the hybrid MEL cell line Hu11. Marker (m) is pBR322×Hinf.

Panel C

5 µg of RNA was analyzed as in panel B, but in addition, a mouse β-maj-globin probe (a 730 bp second exon probe) was added resulting in a 100 nt protected fragment (Mbeta). The probes were of equal specific activity. The activity of the probes was assessed by quantitative agarose, gel electrophoresis and autoradiography of the individual probes before and after mixing for the S1 nuclease analysis (not shown). The positive control is Hu11 Rna (hu). Each probe is individually tested with RNA from Hu11 (hu) or non transgenic mouse fetal liver RNA (ml).

Panel D

Samples of fetal liver (approximately 20 µg) or human red cells were lyzed in 40 µl of H$_2$O and the globin proteins separated as described (Alter et al., 1980). The gel was stained to visualize the globin protein chains. Mouse 9 is an age-matched non-transgenic (litter) mate of mouse 12. The positions of mouse α-, β- and human β-globin are indicated.

Mapping DNaseI Hypersensitive Sites in the Transgenic β-globin Locus

The DNaseI hypersensitive sites flanking the β-globin locus are found in all erythroid tissues studied regardless of which β-like globin is expressed. To determine if the DNaseI hypersensitive sites are reformed in the mini β-locus of transgenic mice expressing high levels of human β-globin mRNA, a DNaseI fadeout was performed on a small sample of the liver and brain of mouse 21 (which has the highest copy number of the β gene mini locus). Limited DNaseI digestion was carried out in the presence of carrier fetal liver or brain nuclei, purified nuclear DNA was recut with BamHI, fractioned, Southern blotted and fragments spanning the whole construct were used as hybridization probes. The 1.15 EcoRI probe which was used to detect the 3' hypersensitive site in HEL and PUTKO cells detects a 17.8 kb BamHI fragment which is due to partial digestion of the BamHI site at the 3' end of the injected fragment. The 17.8 kb BamHI fragment is completely insensitive to limited DNaseI digestion in liver nuclei of mouse 21 (FIG. 7E). The same filter reprobed with a 600 bp AccI 5' human β-globin probe shows that the 2.0 kb BamHI fragment encompassing the 5' end (to −1460 bp) of the highly transcribed human β-globin gene is slightly sensitive to DNaseI digestion, revealing a DNaseI sub-band of approximately 1 kb (FIG. 7D), consistent with a DNaseI hypersensitive site within the β-globin gene promoter (Groudine et al., 1983). Reprobing the same filter with the 0.46 EcoRI GblII probe (FIG. 1C) shows that the 15 kb BamHI fragment encompassing hypersensitive sites 2, 3a, and 4 is exceedingly sensitive to DNaseI digestion in fetal liver nuclei and sub-bands corresponding to cutting at sites 3 and 4 are clearly visible. The same 15 kb BamHI fragment of the transgene mini β locus is insensitive to DNaseI digestion in brain nuclei of the same animal (not shown). The 3.3 kb BamHI fragment (containing hypersensitive site no. 1) of the transgenic mini locus is also very sensitive to DNaseI digestion in liver, but not brain nuclei of mouse 21 (FIG. 7A,B).

In summary, the 5' flanking region is extremely sensitive to DNaseI digestion and has retained the superhypersensitive sites in a tissue specific fashion. Surprisingly, the 3' flanking region is insensitive to DNase digestion and the super hypersensitive site is not retained. The normal hypersensitivity in the promoter is present (Groudine et al., 1983).

Figure 7:
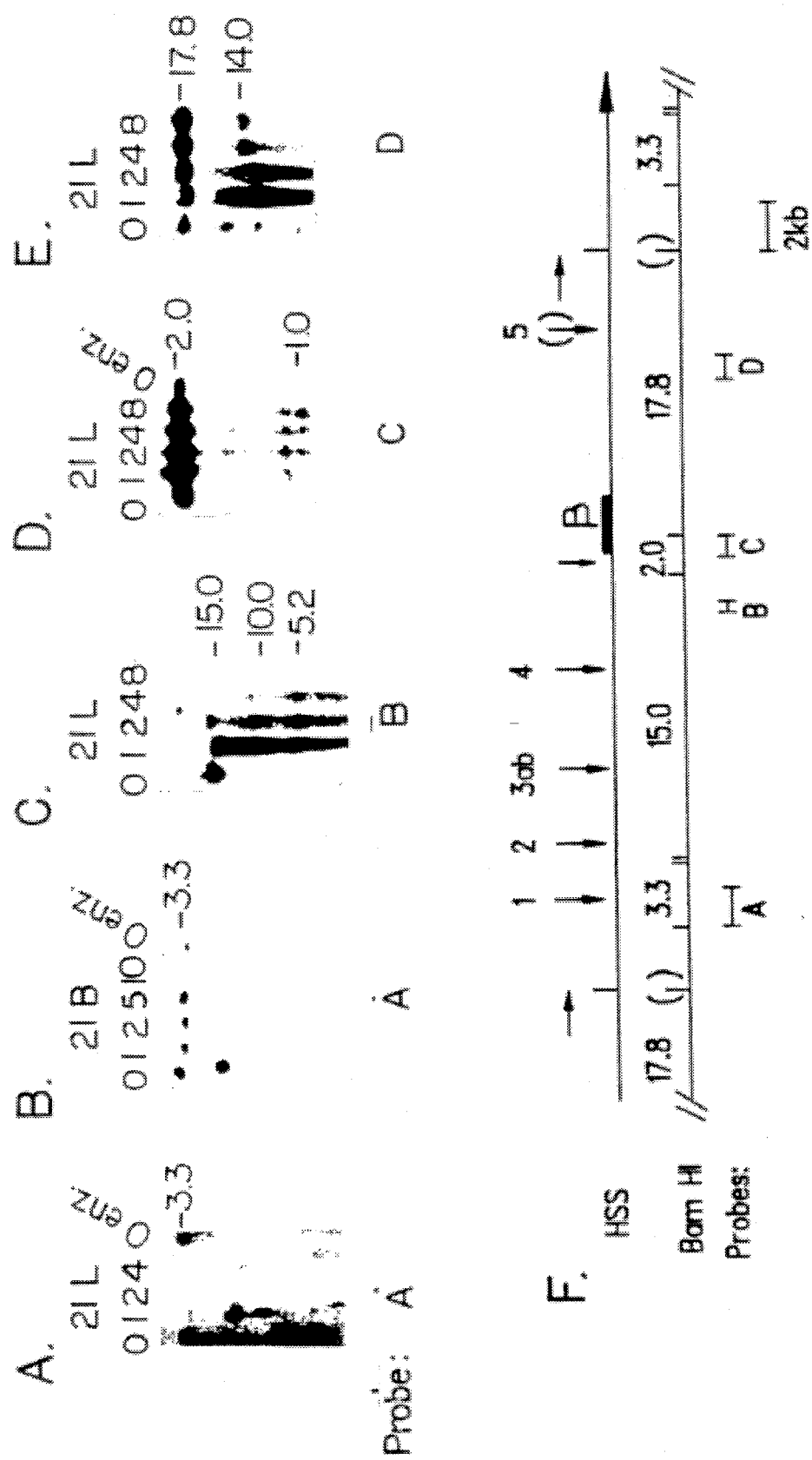
FIG. 7 (A–F) shows the reformation of DNase I hypersensitive sites on the transgenic mini β-globin locus.

In FIG. 7, the experimental details were as follows:

Nuclei of mouse 21 tissues were incubated with 5 μg DNase per ml for 0, 1, 2, 4 and 8 minutes at 37° C. (liver nuclei), or 0, 1, 2, 5 and 10 minutes (brain nuclei). Aliquots of nuclei were incubated for 8 or 10 minutes in the absence of DNase (lanes 0 enz.). Purified DNa was recut with BamHI fractioned on a 0.6% agarose gel, transferred to nitrocellulose and probed with DNA fragments spanning the transgenic human β-globin mini locus (Panels A–E).

The 14.0 kb BamHI fragment detected by probe D in panel E is a junction fragment of the tandem array of the mini β-globin locus. The 17.8 kb band is the result of incomplete BamHI digestion.

Panel F shows a schematic representation of a repeat unit of the mini locus tandem array in mouse 21 on which DNase hypersensitive sites are marked. Site 5 is not reformed in fetal liver nuclei (Panel F). DNaseI sub-bands corresponding to HSS 1 and 2 are not seen in DNaseI fadeout experiments, but the BamHI fragments in which they reside are sensitive to DNaseI digestion in liver (Panels A and C but not brain(Panel B and data not shown).

TABLE 1

Levels of human β-globin RNA and DNA[1]

| Mouse No | β/α RNA[2] | β/Thy-1-DNA[2] | RNA/DNA |
|---|---|---|---|
| 12 | 1.0 | 1.0 | 1.0 |
| 17 | 42.04 | 47.2[3] | 0.9 |
| 21 | N.D.[4] | >100 | N.D. |
| 24 | 0.3 | chimera[5] | N.D. |
| 27 | 10.2 | 11.8 | 0.85 |
| 33 | 0.5 | 0.5 | 1.0 |
| 36 | 10.1 | 8.7 | 1.15 |
| 38 | <0.1 | 0.4 | <0.25 |
| 40 | 7.9 | 7.2 | 1.1 |
| Hull | 0.3 | 0.5 | 0.6 |

[1]All values were normalized to mouse 12 as 1.0 (eg. see FIGS. 4D and 5C) after densitometer scanning of autoradiographs exposed for different times of several experiments.
[2]The ratios were obtained by dividing the human β-globin RNA and DNA signals by those obtained for the mouse α-globin RNA and Thy-1 DNA, respectively. Mouse 34 RNA was measured in only one experiment and not included.
[3]The DNA of mouse 17 was partially degraded (see FIG. 4). We therefore used a low M.W. cross hybridizing band on the Thy-1 blot to quantitate the copy number (rather than the degraded 8kb EcoRI Thy-1 band).
[4]The ratio of human β-globin to mouse globin RNA was not determined (N.D.) accurately in this mouse, due to the very heavy high human to mouse RNA signals (see text).
[5]Mouse 24 is chimeric for the human β-globin gene (FIG. 6) and could therefore not be quantitated.

MATERIALS AND METHODS

Trangenic Mice

The 38 kb SalI fragment was purified from cosmid vector sequences by gel electrophoresis and prepared for injection as described (Kollias et al., 1986; Brinster et al., 1985). Transgenic fetuses were identified by southern blot analysis (Southern, 1975) of placental DNA.

RNA Analysis

RNA extraction of different tissues and S1 nuclease protection analysis were carried out as described previously (Kollias et al., 1986).

DNaseI Sensitivity

DNaseI sensitivity assays were carried out on isolated nuclei as described by Enver et al. (1984), except that 1 mM EGTA was included in all buffers until DNaseI digestion in buffer A plus 1 mM CaCl$_2$ was performed. In the case of transgenic liver and brain, four livers and brains from age-matched normal fetuses were added as carriers to provide sufficient material to carry out the analysis.

Construction of the β-globin Mini Locus (1) A 12 kb BglII fragment (10–22 kb 5' of β-globin) was cloned into the BamHI site of cosmid pTCF (Grosveld et al., 1982) without a ClaI site→cosHG B12.

(2) cosHG B12 was cleaved with Asp718 (13.5 kb 5' of epsilon-globin) and a unique XhoI linker was inserted →cos HG B12X.

(3) cosHG 14.2 (Taramelli et al., 1986) containing the entire epsilon-globin upstream region was also cleaved with DpnI and XhoI linker inserted and packaged→cos HG 14.2X.

(4) A ClaI linker was inserted in the XbaI site of pUC18→ pUC18C.

(5) The 4.7 kb BglII fragment containing the β-globin gene was inserted in the BamHI site of pUC18C→puC18C-BG.

(6) A 12 kb HpaI-BamHI fragment (12–24 kb 3' of β-globin) was cloned into HpaI-BamHI of cosmid pTCF lacking a Cla site→cos HG HB12.

(7) The final cosmid construct was put together as a four fragment ligation and packaging, a 16.5 kb PvuI-XhoI fragment from cos HG b12X containing the cosmid and part of the upstream sequences, an 11 kb XhoI-ClaI fragment from cos HG 14.2X containing the remainder of the upstream sequences, a 4.7 kb ClaI-KpnI fragment from pUC18C-BG containing the β-globin gene and a 19 kb KpnI-HpaI fragment from cos HG HB12 containing the 3' flanking region and the second cosmid for packaging purposes→cos HG "mini" locus (FIG.3).

Discussion of Example 1

Position Effect Independent Expression

The introduction of the human β-globin gene flanked by the upstream and downstream regions in transgenic mice has resulted in an expression pattern that is position independent and directly related to copy number, with levels of human β-globin mRNA as high mouse β-globin mRNA. This is different from that observed with previous transgenic mice using the β-globin gene alone (Magram et al., 1985; Chada et al., 1985; Townes et al., 1985; Kollias et al., 1986, 1987), or other genes such as the immunoglobulin genes (Grosschedl et al., 1984), albumin genes (Pinkert et al., 1987) Thy-1 gene (Kollias et al., 1987) AFP gene (Hammer et al., 1987) and many others. As a result of position effects in all transgenic mice experiments to date, the level of transgenic expression has been suboptimal and has varied between different mice, i.e. there has been no strict correlation between the copy number of the transgene and the level of expression. Therefore, it has been very difficult to quantitate any experiments accurately and, as a result, it has been impossible, for example, to examine the co-operation between regulatory elements in any gene. The results described in this example indicate that this problem can be overcome for the β-globin gene. It is clear that the expression levels found in mice containing the intact mini locus is directly proportional to the number of genes that have been incorporated (Table I). In addition, the expression level per human β-globin gene in all of those mice is very similar to that observed for the endogenous mouse β-globin gene (FIG. 5). It is therefore concluded that the β-globin locus flanking sequences confer position independent expression on the β-globin gene which itself is erythroid specific. In addition it is concluded that all of the regulatory sequences involved in β-globin gene expression are included in this construct.

Gene Therapy

Perhaps the most interesting application for the properties of the dominant control region(s) is that they might allow completely regulated expression of the β-globin (and possibly other genes) in retroviral vector or transfection systems. Gene expression in such systems is presently position dependent and inefficient. In particular, retroviral vector systems which are presently the only efficient way to transfer genes into hematopoietic (or other) stem cells, are very sensitive to the integration site of the retroviral vector (Cone et al., 1987). Inclusion of the globin dominant control regions may solve this problem and allow the efficient transfer of a fully active, single copy human globin gene to hematopoietic stem cells. This would form the basis for gene therapy by gene addition in the case of thalassemias.

EXAMPLE 2

A β-globin "micro locus" was constructed including all four of the five 5' DNaseI superhypersensitive sites (HSS). The method described below is general and the micro locus produced shows an advantageous increase in expression levels. The method described below may therefore be applied to the construction of other micro loci from dominant activator regions of other genes.

Methods for the Construction of a β-globin Micro Locus

Figure 8:
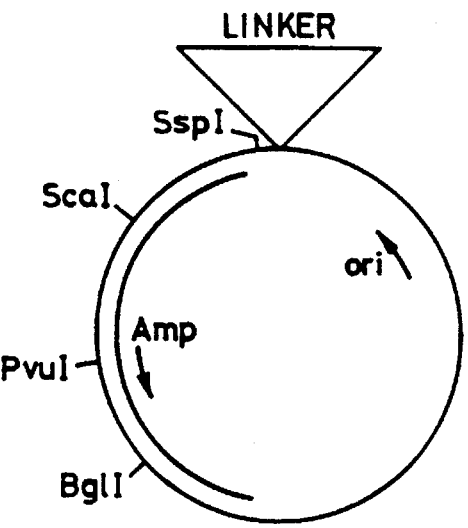
FIG. 8 shows the construction of plasmids GSE1364, 1365 and 1366.
Figure 8:
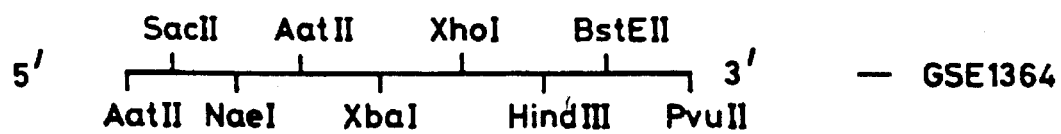
Figure 8:
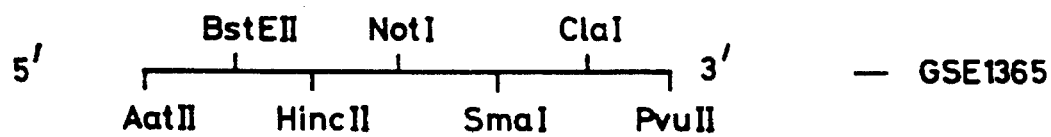
Figure 8:
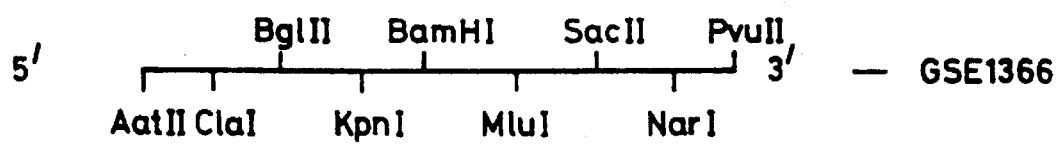

To facilitate DNA manipulations required to place all four 5' DNaseI hypersensitive sites and the human β-globin gene in a vector containing the tk neo gene, a series of polylinker vectors were constructed by inserting oligonucleotides between the Aat II and Pvu II sites of the plasmid vector pUC 18 to generate plasmids GSE 1364, GSE 1365, and GSE 1366 (see FIG. 8). The required DNA fragments were cloned into the unique restriction sites created in the different polylinker vectors. In particular:

1. A 2.1 kb XbaI—XbaI fragment encompassing DNase HS1 was cloned into the XbaI site of GSE 1364, 2. A 1.9 kb Hind III—Hind III fragment was cloned into the Hind III site of the plasmid carrying HS1 to give a plasmid carrying HSS 1 and 2 in the same orientation as that found in the normal human β-globin locus, 3. A 1.5 kb Asp718-SalI fragment encompassing DNaseI HSS 3 was made blunt-ended by treatment with Klenow fragment of DNA polymerase deoxynucleoside triphosphates and cloned into the HindII site of GSE 1365, 4. A 1.1 kb partial SacI fragment encompassing DNaseI HSS4 was similarly made, blunt-ended and cloned into the SmaI site of the plasmid carrying HSS3 to give a plasmid with HSS3 and HSS4 in the same orientation as that found in the normal human β-globin locus, 5. The 4.9 kb BglII fragment containing a normal copy of the human β-globin gene with 1.56 kb of 5' flanking sequence and 1.84 kb of 3' flanking sequence was cloned into the BamHI site of GSE 1366, 6. A 2.0 kb partial NarI fragment which includes the Herpes Simplex Virus (HSV) thymidine kinase (tk) promoter driving the expression of the Tn5 neomycin resistance gene and 3' polyadenylated sequences of the HSV tk gene was cloned into the NarI site of the plasmid carrying the human β-globin gene and, 7. The four HSS, the human β-globin gene and the tkneo gene were combined in a three fragment ligation using a PvuI-BstEII fragment of HSS 1 and 2 with a BstEII ClaI fragment of HSS 3 and 4 and a ClaI-PvuI fragment of the plasmid containing the β-globin and tkneo genes.

The final construct was shown to direct high-level expression of the human β-globin gene in mouse erythroleukemic cells (MEL) independent of the position of integration of the DNA in the host cell chromosome. The level of β-globin expression was related to the gene copy number.

EXAMPLE 3

To test the effect of changing the position of the DNaseI HSS relative to the β-globin gene, the DNaseI HSS fragments described in Example 2 above were cloned so as to give a 6.5 kb NotI restriction fragment. This DNA fragment was cloned in both orientations into a unique NotI site in two different plasmids containing the tkneo gene as a 2.7 kb partial EcoRI fragment and the human β-globin gene as a 4.9 kb BglII fragment as described above.

Figure 9:
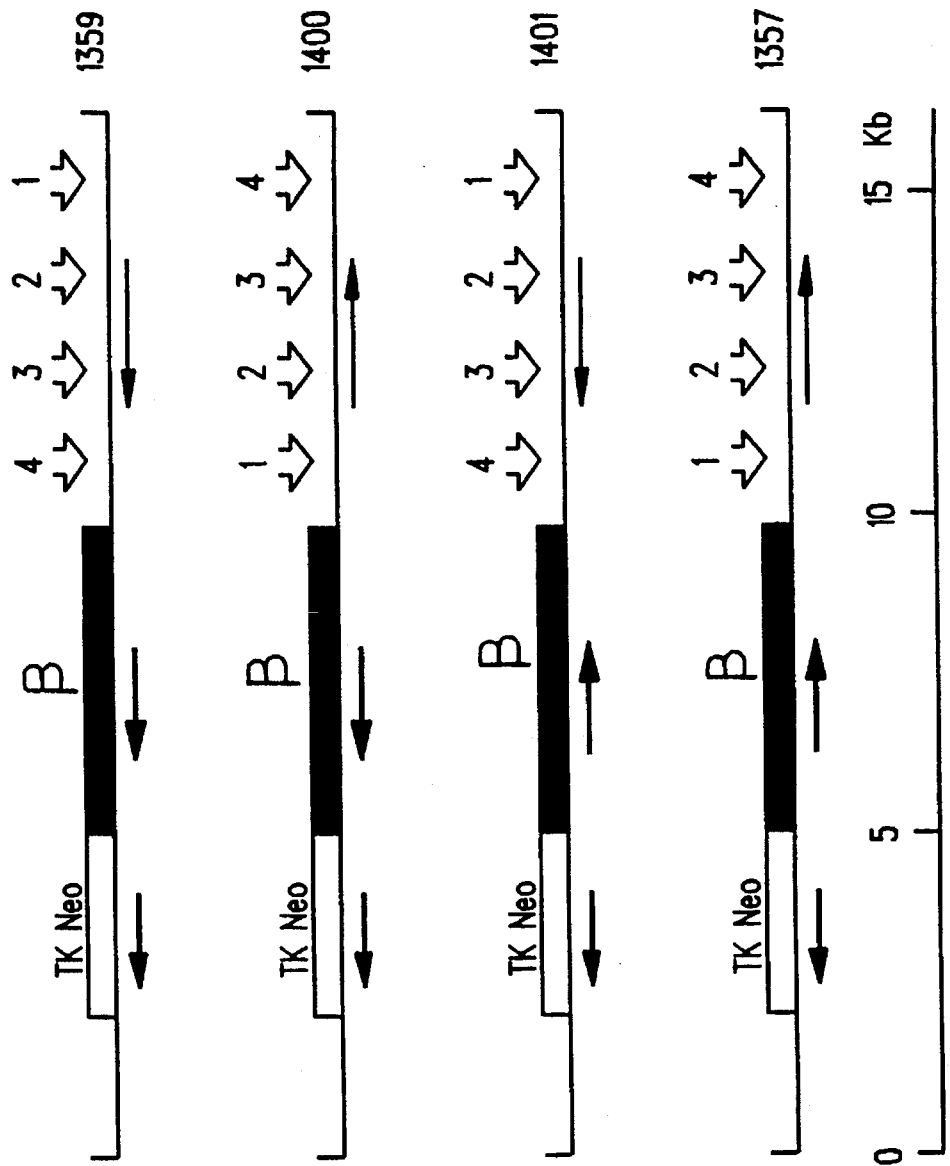
FIG. 9 shows the construction of plasmids GSE1359, 1400, 1401 and 1357.

The two tkneo β-globin plasmids differed in the orientation of the β-globin gene and cloning of the 6.5 kb NST I fragment in both orientations generated the four plasmids GSE 1359, GSE 1400, GSE 1401 and GSE 1357 shown in FIG. 9.

The DNA of the four plasmids shown in FIG. 9 was linearized by digestion with the restriction enzyme PvuI. The DNAs were recovered by ethanol precipitation and introduced into MEL cells growing exponentially in alpha MEM medium supplemented with 10% fetal calf serum and antibiotics.

MEL cells (approx. $10^7$) were collected by centrifugation (1000 g for 10 minutes) washed once with ESB Buffer (20 mM HEPES pH 7.0, 140 mM NaCl, 5 mM KCl) and resuspended in 1 ml of ESB containing 100 µg of linearized plasmid DNA. After incubation on ice for 10 minutes, cells were placed in a well of a 24 well tissue culture plate (Nunc) and a 10 ms shock was delivered using a Haeffer "Pro genitor" electroshock apparatus at a voltage gradient of 250 volts/cm (Antonious et al EMBO J, (1988), 7, 377–384).

Cells were recovered into 40 ml of αMEM and 10% fetal calf serum at 37° C. for 24 hours and G418 selection was applied by changing the tissue culture medium for αMEM with 10% fetal calf serum and 800 mg G418 (Gibco BRL) per ml. After 11 days in selection G418 resistant cell populations were harvested by centrifugation. RNA and DNA was prepared and part of the culture was induced to undergo erythroid differentiation by growth in αMEM with 10% fetal calf serum and 2% dimethyl sulfoxide (DMSO-BDH). After four days, populations were harvested and RNA prepared by homogenizing cells in 3M L:Cl 6M urea.

After sonication and incubation at 4° C. overnight, RNA was precipitated and analysed by Northern blot analysis. RNA from uninduced (−) or induced (+) MEL cell populations (10 mg) was denatured with 50% formamide 15% formaldehyde in 1×MOPS buffer heated at 60% for 10 minutes, chilled on ice and loaded on to a 1% agarose gel. The gel was run at 70 volts/cm for 8 hours in 1×MOPS buffer (20 mM MOPS pH7, 5 mm sodium acetate 20 mM EDTA). The gel was soaked in 20×SSC (3 M NaCl 0.15M trisodium citrate) for 30 minutes then blotted directly to a nitrocellulose filter (Schleicher and Schuller—0.1 µM) overnight. The filter was baked for 2 hours at 80° C. then hybridized to DNA probes labelled to high specific activities by Nick translation (Rigby et al, J. Mol Biol. (1977) 113 237–251).

Figure 10:
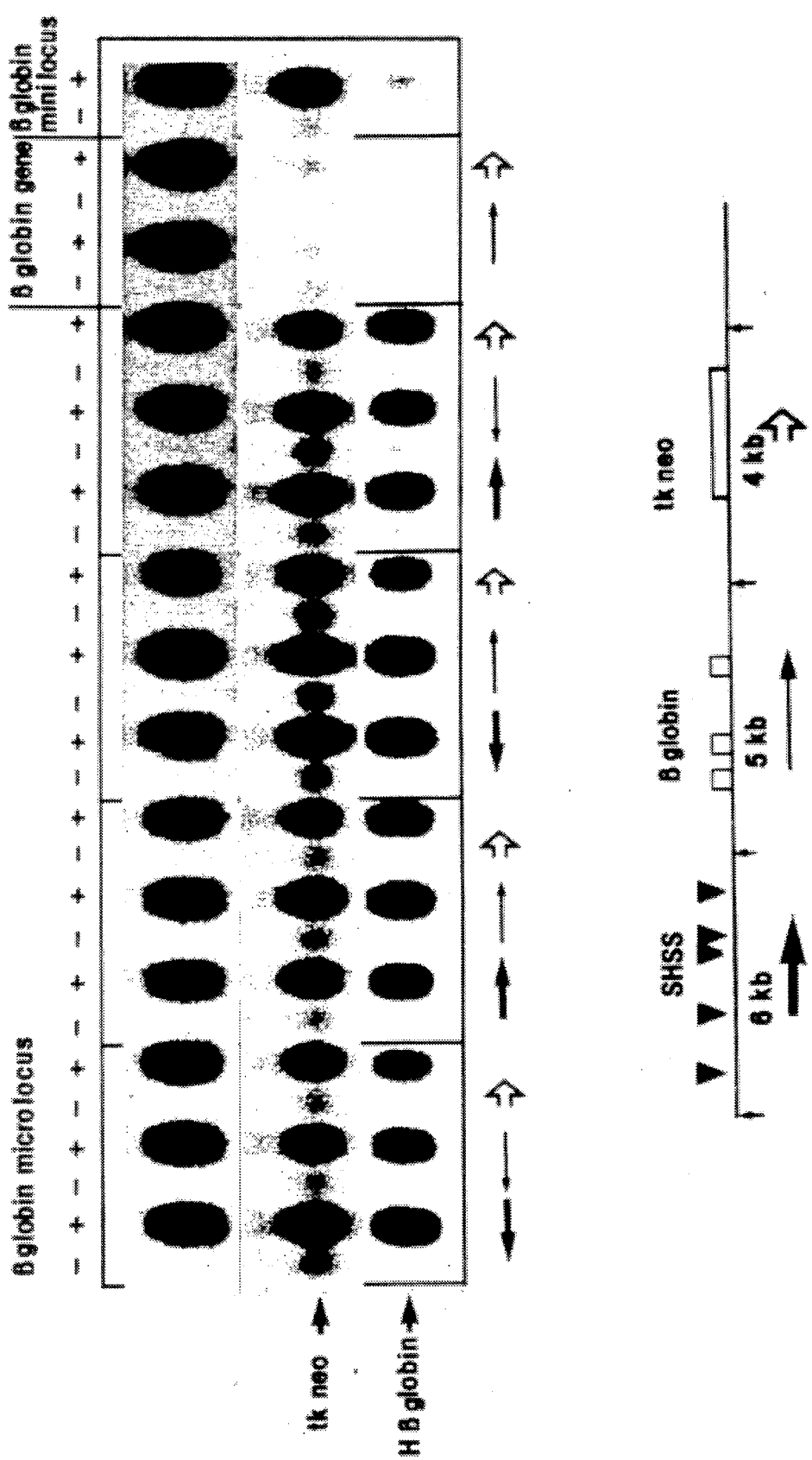
FIG. 10 shows human β-globin expression.

Hybridization was performed in buffer containing 50% formamide, 6×SSC, 10×Denhardts 1% SDS and 200 µg salmon sperm DNA per ml (Lang et al EMBO J (1988), 7(6), 1675–1682). After overnight hybridization at 42° C., filters were washed to a final stringency of 0.1×SSC 0.1% SDS at 55° C. Filters were exposed to x ray film with intensifying screens at 70° C. Specific DNA probes used in the experiments of FIG. 10 were:

Human β-globin

A 800 bp EcoRI-MspI fragment which includes the 3rd exon of the human β-globin gene.

Mouse α-globin

A 300 bp BamHI fragment of the mouse α-globin gene including sequences from the 2nd exon.

tkneo

A 2.0 kb partial Nar I fragment encompassing the tk promoter and the Neo resistance gene.

Mouse Histone H4 Gene

A 300 bp HinfI fragment of a mouse histone H4 gene.

The experiment described above shows that:

1. Human β-globin RNA expression in induced MEL cells is as high or higher than the expression of endogenous mouse α-globin genes, 2. β-globin expression using β micro locus constructs is higher than that obtained with a β mini locus in MEL cells, 3. The dominant activator sequences increase transcription from the tkneo gene approximately 100 fold compared to plasmids that do not contain the dominant activator sequences and 4. The dominant activator sequence works on the human β-globin gene in both orientations upstream or downstream of the β-gene.

EXAMPLE 4

Experiments were conducted to identify any dominant activator sequences in the human CD2 gene and to test their ability to direct integration site independent expression. Two DNaseI hypersensitive sites were found 3' of the human CD2 gene which is expressed at a high level in the thymus of transgenic mice. A 5.5 kb BamHI-XbaI fragment of CD2 3' sequence including the DNaseI HSS was clone next to a 4.8 kb BglII human β-globin gene fragment (Example 5 below) or a 9.5 kb mouse/human hybrid Thy-1 gene fragment. DNA fragments prepared from βCD2 and Thy-1 CD2 constructs were introduced into fertilized mouse eggs. Transgenic mice with a range of copy numbers were obtained and analysis showed high-level expression of human β-globin (example 5) and mouse/human hybrid Thy-1 gene mRNA in thymus (this example) which was related to copy number and independent of the site of integration into the mouse genome.

The experiments described in this Example and in Example 5 demonstrate unequivocally the presence of a dominant activator sequence in the 5.5 kb BamHI-XbaI fragment 3' of the human CD2 gene.

Mapping DNase HSS in the CD2 Gene

Transgenic mice carrying the 2.8 kb KpNI fragment of the human CD2 gene were sacrificed and nuclei prepared from thymus and liver of mouse lines CD2-4 and CD2-1 (Lang et al, EMBO J, (1988), 7(6), 1675–1682). DNaseI digestions were performed as described herein (see also Grosveld et al, Cell, (1988), 51, 975–985).

Figure 11:
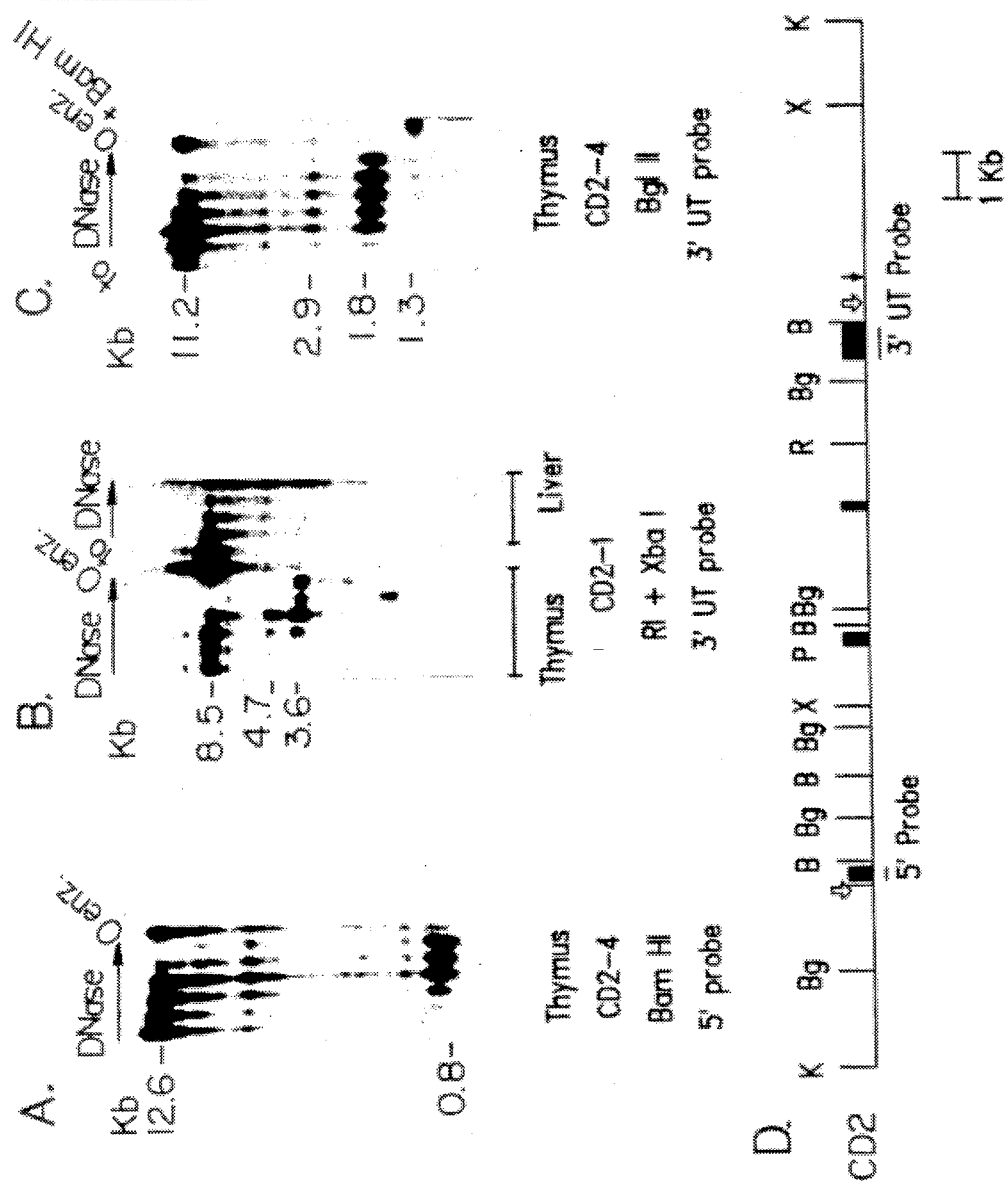
FIG. 11 (A–D) shows the mapping of DE2 hypersensitive sites.

DNA samples were recut with the restriction enzymes indicated in FIG. 11 and probed with 5' or 3' human CD2 probes. Strong DNaseI HSS were present 5' of the gene and two 3' sites are seen 3' of the CD2 gene only in transgenic thymus not in liver nuclei.

Figure 12:
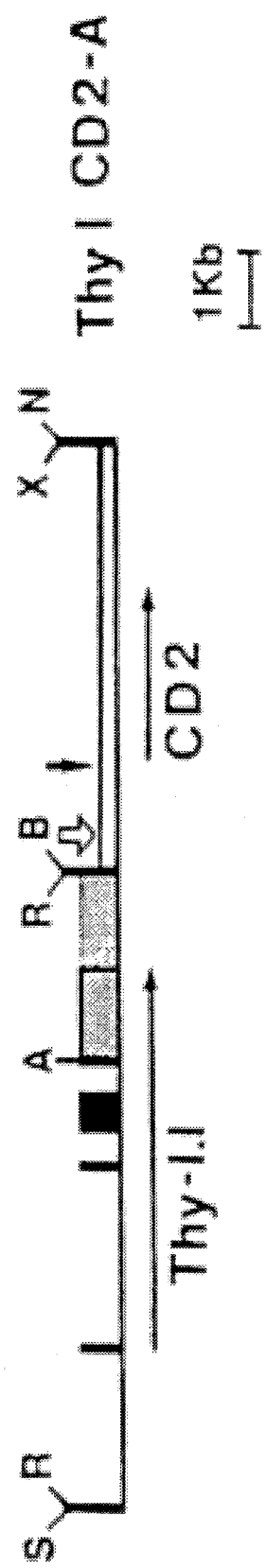
FIG. 12 shows a Thy-1 CD2 construct.

FIG. 12 shows a Thy-1.1 CD2 construct. The stippled bar denotes human Thy-1 sequences and the two arrows show the position of the DNaseI HSS in the CD2 fragment.

A 5.5 kb BamHI-XbaI fragment 3' of the human CD2 gene shown to contain the two 3' DNase I HSS was cloned between the BamHI and XbaI sites of the blue script vector KS+ (Promega). A 9.5 kb EcoRI fragment containing a mouse-human hybrid gene (Kollias et al, cell, (1987), 51, 21–23), was cloned into the EcoRI site next to the 5.5 kb BamHI-XbaI fragment to give the plasmid Thy-1 CD2-A shown in FIG. 12. Plasmid sequences were removed by digestion with restriction endonucleases SalI and Not I and the 15 kb Thy-1 CD2 insert was purified by gel electrophoresis and passage over an Elutip D column (Schleicher and Schuell).

The purified DNA was introduced into the nuclei of fertilized CBA×C57 BL-10 mouse eggs by microinjection (Lang et al, EMBO J (1988), 7, 1675–1682). Injected eggs were transplanted into the oviduct of pseudo pregnant foster mothers by standard techniques (Hogan et al, "Manipulating the mouse embryo" Cold Spring Harbor publications (1986)). Transgenic mice were identified by Southern blot analysis of tail DNA as described previously (Lang et al Loc cit) and tissues were dissected for RNA preparation when animals were 3 to 4 weeks old.

Figure 13:
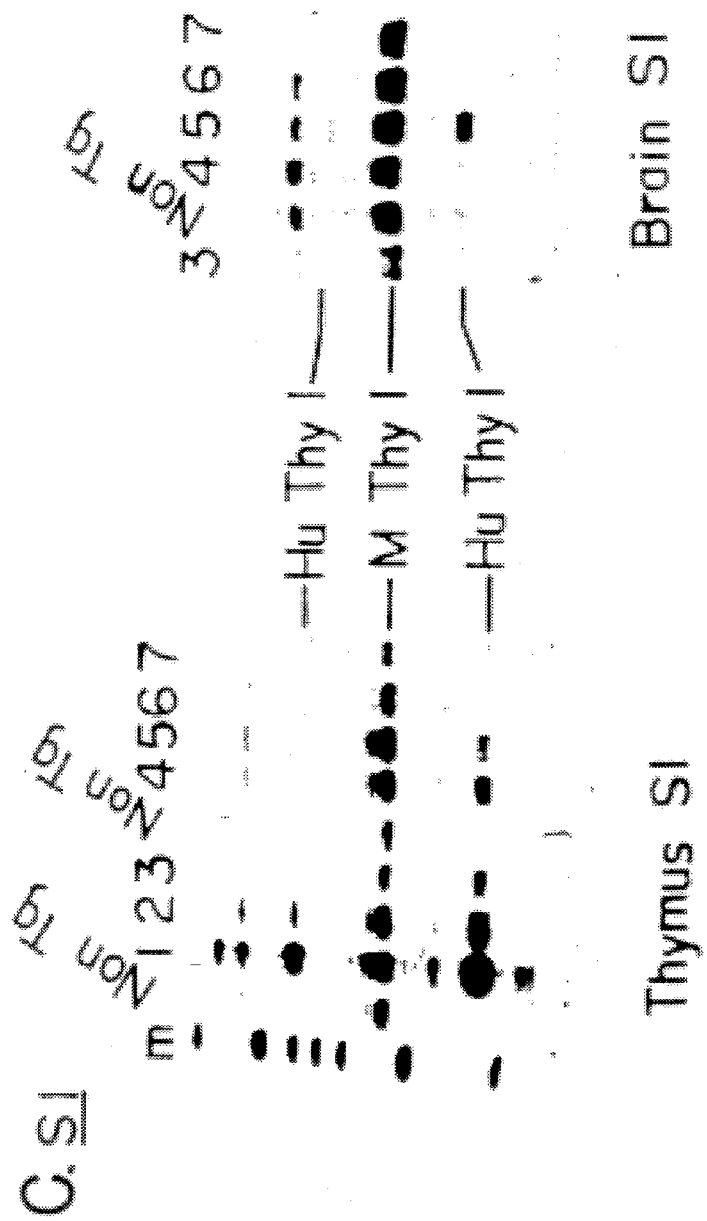
FIG. 13 shows the distribution of Thy-1 in the thymus and brain of transgenic mice.

Referring to FIG. 13 RNA from thypus or brain of transgenic mice 1, 2, 3 5, 6, 7 and 8 (5 µg) was hybridized with a 5' end labelled Tth III-Sac I mouse Thy-1 IVth exon probe and a 3' end labelled BglII Neo I human Thy-1 probe at 52° C. for 12 hours after melting the probes or RNA at 85° C. for 15 minutes.

RNA DNA hybrids were digested with Nuclease S1 (Boehringer Mannheim) as described previously Kollias et al Cell, (1988), 51, 21–31) and protected fragments run out on a 5% polyacrylamide 8M urea sequencing gel. The positions of protected fragments for endogenous mouse and transgenic mouse human Thy-1 RNAs are indicated.

The level of expression per gene copy of the hybrid mouse human Thy-1 gene in transgenic thymus is as high as that for the endogenous Thy-1 gene and is related to the gene copy number (mouse 1 has approximately 20 copies of the transgene-mice 2 has 10 copies of the transgene).

EXAMPLE 5

Figure 14:
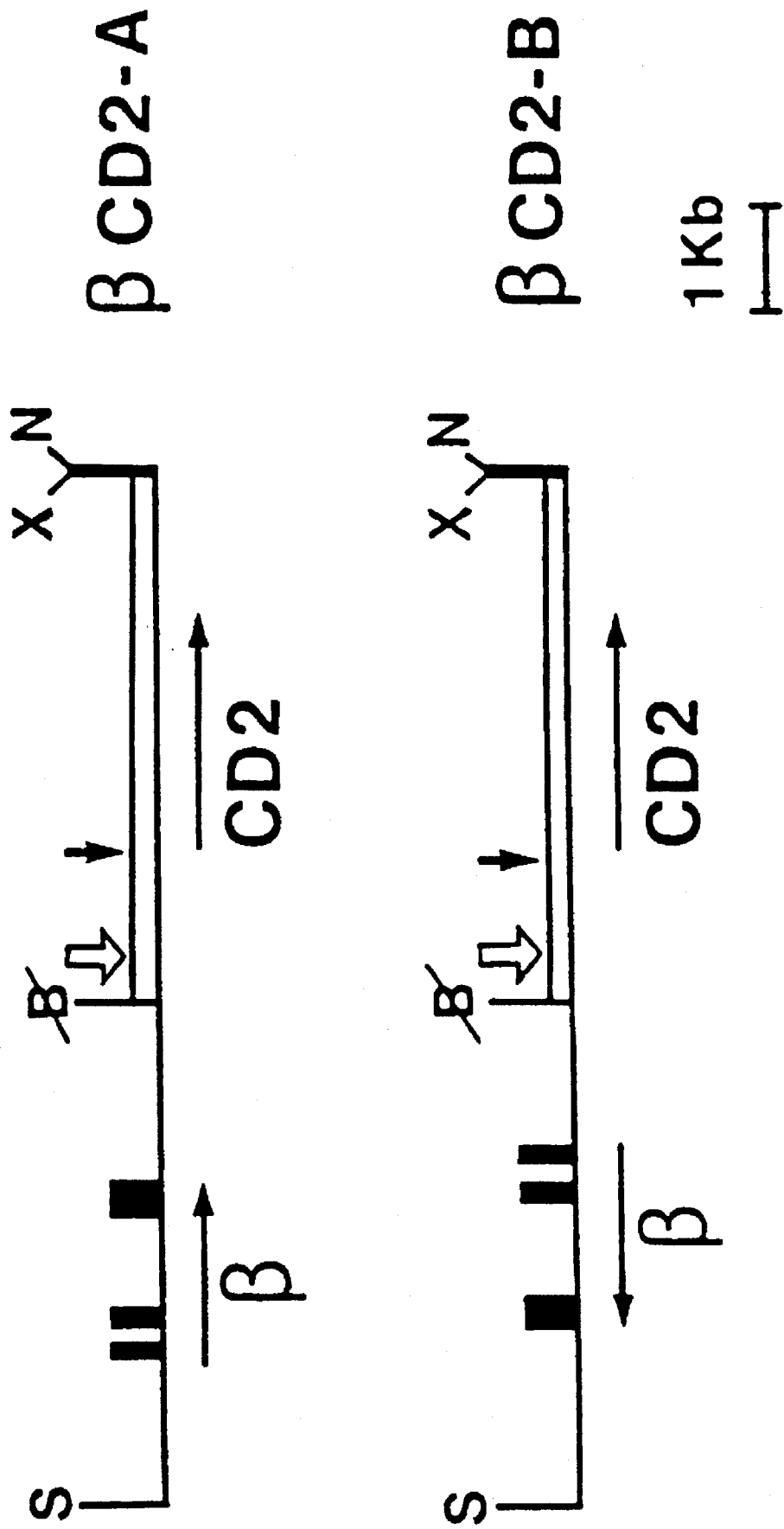
FIG. 14 (A–B) shows the construction of a β-globin CD2 construct.

This example refers to FIG. 14 which shows the construction of a β-globin CD2 plasmid.

β-globin CD2 expression in transgenic mice was brought about using dominant activator sequences of the invention.

The inserts of plasmid βCD2-A and β-CD2-β were isolated by agarose gel electrophoresis after digestion with restriction enzymes Nat I and Sal I. DNA was injected into nuclei of fertilized mouse eggs as described above (see also Grosveld et al, cell (1987), 51 975–985. Transgenic mice were identified by Southern blot analysis of tail DNA using a human β-globin indicator probe (900 bp BamHI-EcoRI fragment).

Figure 15:
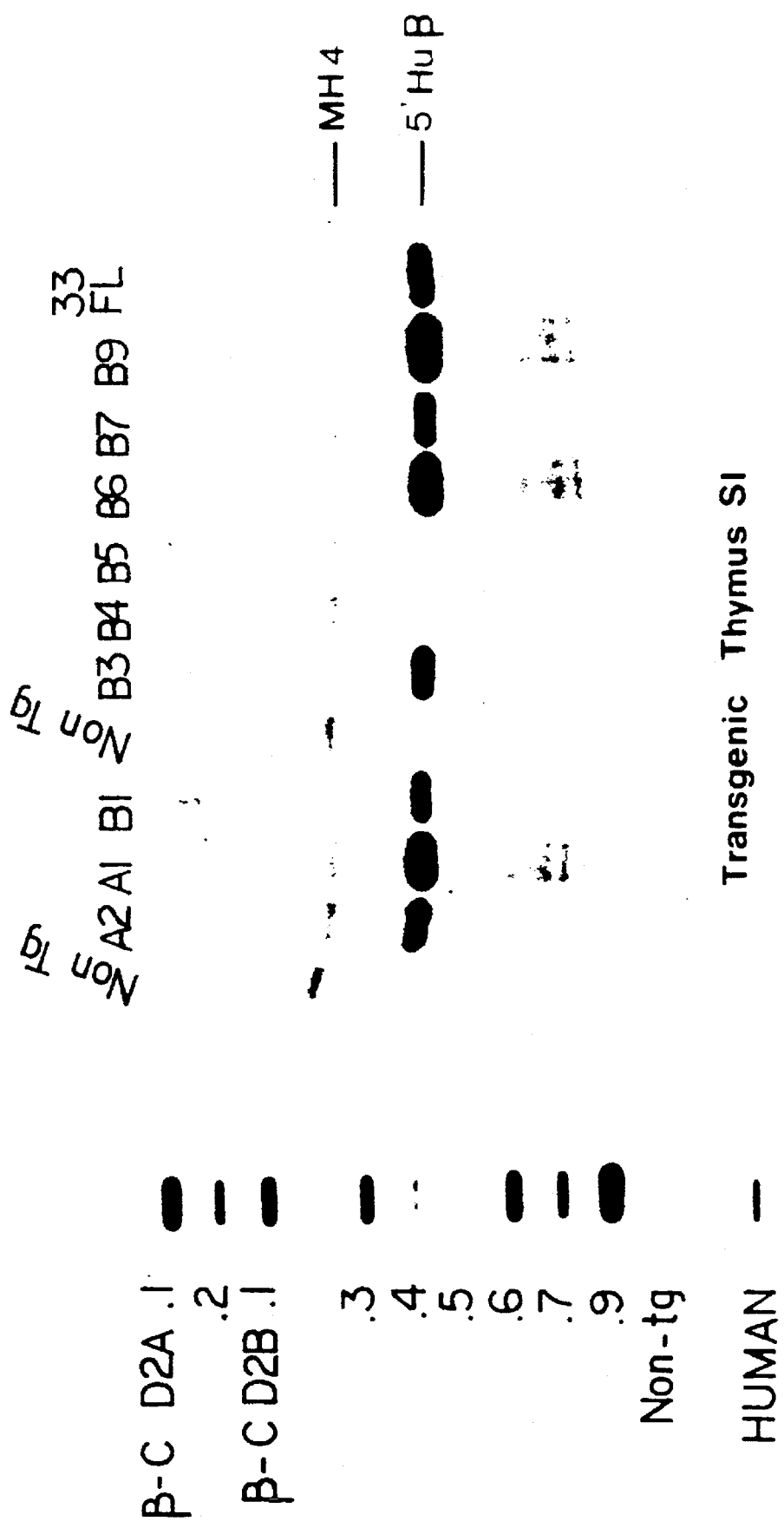
FIG. 15 shows the genomic DNA of transgenic mice carrying the construct of FIG. 14.

FIG. 15 shows 5 mg of genomic DNA from transgenic mice carrying either the βCD2-A or βCD2-β construct applied to a nitrocellulose filter using a slot blot manifold (Schleicher and Scheull). The filter was hybridized to a nick-translated β-globin 2nd intron probe and washed to a final stringency of 0.1×SSC 0.1% SDS at 65° C. The strength of the hybridization signal is a direct measure of the number of gene copies on each mouse.

FIG. 15B shows an S1 Nuclease analysis of thymus RNA prepared from transgenic mice. RNA (1 mg) was hybridized with a 5' end labelled 52.5 bp AccI fragment of a β-globin CDNA construct (Grosveld et al, cell, (1987), 51, 975–985) and a 300 bp Hinf I fragment of a mouse histone H4 gene as an internal control.

After hybridization at 52° C. for 12 hours, samples were digested with Nuclease S1 and protected fragments analysed on a 5% polyacrylomide 8M urea gel. The positions have protected fragments for endogenous histone H4 and human β-globin mRNA are indicated. The intensity of the human β-globin-protected fragment is a direct measure of the amount of human β-globin mRNA transcribed in the thymus. For comparison 0.1 mg of fetal liver RNA from a transgenic mouse carrying 4 copies of the β-micro locus was used in the track labelled 33 FL.

Referring to FIG. 14, the 5.5 kb BamHI-XbaI fragment of human CD2 gene was cloned between the BamHi and XbaI sites of the bluescript vector KS+ (promega). The 4.9 kb BglII fragment of the human β-globin gene was cloned into the BamHI site of this plasmid in both orientations (βCD2A and βCD2-β). The vertical arrows indicate positions of CD2 DNaseI HSS. The black bars donate exons of the human β-globin gene and horizontal arrows show the orientation of the gene fragments used.

It will be understood that the invention is described by way of example only and modifications may be made within the scope of the invention.

REFERENCES

Alter, B., Goff, S., Efremor, G., Gravley, M. and Huisman, T. (1980) Globin chain electrophoresis: a new approach to the determination of the $^G\gamma/^A\gamma$ ratio in foetal haemoglobin and to the studies of globin synthesis. Brit. J. Haematol. 44, 527–534.

Angel, P., Imagawa, M., Chin, R., Stein, B., Imbra, R., Rahmsdorf, M., Jonat, A., Herrlich, P. and Karin, M. (1987) Phorbol ester-inducible genes contain a common cis element recognized by a TPA-mediated transacting factor. Cell 49, 729–739.

Behringer, R. R., Hammer, R. E., Brinster, R. L., Palmiter, R. D. and Townes, T. M. (1987) Two 3' sequences direct erythroid-specific expression of human β-globin genes in transgenic mice. Proc. Natl. Acad. Sci. U.S.A. (in press)

Brinster, R. L., Chan, H. Y., Trumbauer, M. E., Yagle, M. K. and Palmiter, R. D. (1985) Factors affecting the efficiency of introducing foreign DNA into mice by microinjecting eggs. Proc. Natl. Acad. Sci. U.S.A. 82, 4438–4442.

Chada, K., Magram J., Raphael, K., Radice, G., Lacy, E. and Costantini, F. (1985) Specific expression of a foreign β-globin gene in erythroid cells of transgenic mice. Nature 314, 377–380.

Charnay, P., Treisman, R., Mellon, P., Chao, M., Axel, R. and Maniatis, T. (1984) Differences in human α- and β-globin gene expression in mouse erythroleukemia cells: the role of intragenic sequences. Cell 33, 251–263.

Choi, O-R. and Engel, J. D. (1986) A 3' enhancer is required for temporal and tissue specific transcriptional activation of the chicken adult beta-globin gene. Nature 323, 731–734.

Cockerhill, P. and Garrard, W. (1986) Chomosomal loop anchorage of the kappa Ig gene locus next to the enhancer in a region containing topoisomerase II sites. Cell 44, 273–282.

Collins, F. S. and Weissman, S. M. (1984) The molecular genetics of human hemoglobin. Prog. Nucl. Acid Res. Mol. Biol. 31, 315–462.

Cone, R. D., Benarous, W. W., Baorto, D. and Mulligan, R. C. (1987) Regulated expression of a complete human β-globin gene encoded by a transmissible retrovirus vector. Mol Cell. Biol. 7, 887–897.

Curtin, P. and Kan, Y. W. (1986) A normal β-globin gene is inactivated by a large distant deletion. In: Hemoglobin Switching. Fifth Conference on Hemoglobin Switching, Washington. Ed. G. Stamatoyannopoulos, Alan R. Liss Inc., New York, 1987, in press.

Enver, T., Brewer, A. C. and Patient, R. K. (1985) Simian Virus 40-mediated cis induction of the Xenopus β-globin DNaseI hypersensitive site. Nature 318, 680–683.

Gasser, S. and Laemmli, U. (1986) Cohabitation of scaffold binding regions with upstream/enhancer elements of three developmentally regulated genes of D. melanogaster. Cell 46, 521–530.

Grosschedl, R., Weaver, D., Baltimore, D. and Costantini, R. (1984) Introduction of a μ Ig gene into mouse germline: Specific expression in lymphoid cells and synthesis of functional antibody. Cell 38 647–658.

Grosveld, F. G., Lund, T., Murray, E. J., Mellor, A. L., Dahl, H. H. M. and Flavell, R. A. (1982) The construction of cosmid libraries which can be used to transform eukaryotic cells. Nucl. Acid Res. 10, 6715–6732.

Groudine, M., Kohwi-Shigematsu, T., Gelinas, R., Stamatayannopoulos, G. and Papayannopoulou, T. (1983) Human fetal to adult hemoglobin switching: changes in chromatin structure of the β-globin locus. Proc. Natl. Acad. Sci. U.S.A. 80, 7551–7555.

Hammer, R., Krumlauf, R., Campen, S., Brinster, R. and Tilghman, S. (1987) Diversity of α-fetoprotein gene expression in mice is generated by a combination of separate enhancer elements. Science 235, 53–58.

Hesse, J. E., Nickol, J. M., Lieber, M. R. and Felsenfeld, G. (1986) Regulated gene expression in transfected primary chicken erythrocytes. Proc. Natl. Acad. Sci. U.S.A. 83, 4312–4316.

Hock, R. A. and Miller, A. D. (1986) Retrovirus-mediated transfer and expression of drug resistance genes in human haematopoietic progenitor cells. Nature 320, 275–277.

Kioussis, D., Vanin, E., deLange, T., Flavell, R. A. and Grosveld, F. G. (1983) β-globin gene inactivation by DNA translocation in γβ-thalassaemia. Nature 306, 662–666.

Klein, G., Zeuthen, J., Eriksson, I., Tekasaki, P., Bernoco, M., Rosen, A. Masucci, G., Povey, S. and Ber, R. (1980) Hybridization of a myeloid leukaemia derived human cell line (K562) with a Burkitt's Lymphoma line. J. Natl. Canc. Inst. 64, 725–738.

Kollias, G., Hurst, J., deBoer, E. and Grosveld, F. (1987) A tissue and developmental specific enhancer is located downstream from the human β-globin gene. Nucl. Acids Res. 15, 5739–5747.

Kollias, G., Wrighton, N., Hurst, J. and Grosveld, F. (1986) Regulated expression of human $^A\gamma$-, β-, and hybrid γβ-globin genes in transgenic mice: Manipulation of the developmental expression patterns. Cell 46, 89–94.

Lawson, G., Knoll, B., March, C., Woo, S., Tsai, M. and O'Malley, B. (1982) Definition of 5' and 3' structural boundaries of the chromatin domain containing the ovalbumin multigene family. J. Biol. Chem. 257, 1501–1507.

Lee, W., Mitchell, P. and Tjian, R. (1987) purified transcription factor AP-1 interacts with TPA-inducible enhancer elements. Cell 44, 273–282.

Magram, J., Chada, K. and Costantini, F. (1985) Developmental regulation of a cloned adult β-globin gene in transgenic mice. Nature 315, 338–340.

Maniatis, T., Fritsch, E. F., Lauer, J. and Lawn, R. M. (1981) Molecular genetics of human hemoglobins. Ann. Rev. Genet. 14, 145–178.

Martin, P. and Papayannopoulou, T. (1982) HEL cells: A new human erythroleukemia cell line with spontaneous and induced globin expression. Science 216, 1233–1235.

Nicholls, R., Fischel-Ghodsian, N. and Higgs, D. (1987) Recombination at the human α-globin gene cluster: sequence features and topological constraint. Cell 49, 369–378.

Palmiter, R. D. and Brinster, R. L. (1986) Germ-line transformation of mice. Ann. Rev. Genet. 20, 465–499.

Pinkert, C., Ornitz, D., Brinster, R. and Palmiter, R. (1987) An enhancer located 10 kb upstream functions along with its promoter to direct efficient, liver-specific expression in transgenic mice. Genes and Devel. 1, 268–278.

Southern, E. M. (1975) Detection of specific sequences among DNA fragments separated by gel electrophoresis. J. Mol. Biol. 98, 503–517.

Taramelli, R., Kioussis, D., Vanin, E., Bartram, K., Groffen, J., Hurst, J. and Grosveld, F. G. (1986) γδβ-thalassaemias 1 and 2 are the result of a 100 kbp deletion in the human β-globin cluster. Nucl. Acids Res. 14, 7017–7029.

Townes, T. M., Lingrel, J. B., Chen, H. Y., Brinster, R. L. and Palmiter, R. D. (1985) Erythroid specific expression of human β-globin genes in transgenic mice. EMBO J. 4, 1715–1723.

Tuan, D., Solomon, W., Qiliang, L. S. and Irvin, M. L. (1985) The "β-like-globin" gene domain in human erythroid cells. Proc. Natl. Acad. Sci. U.S.A. 32, 6384–6388.

van der Ploeg, L. H. T., Konings, A., Oort, M., Roos, D., Bernini, L. and Flavell, R. A. (1980) γβ-thalassaemia: deletion of the γ- and δ-genes influences β-globin gene expression in man. Nature 283, 637–642.

Wright, S., Rosenthal, A., Flavell, R. A. and Grosveld, F. (1984) DNA sequences required for regulated expression of β-globin genes in murine erythroleukemia cells. Cell 38, 265–273.

Zavodny, P., Roginsky, R. and Skoultchi, A. (1984) In: Globin gene expression and hematopoietic differentiation. Eds. Stamatoyannopoulos, G. and Nienhuis, A.) Alan R. Liss Inc., New York, pp. 53–62.

I claim:

1. An isolated DNA molecule, comprising:

(i) a dominant activator sequence that is specific for a particular mammalian cell-type, (ii) a promoter that is functional in said particular mammalian cell-type, and (iii) a structural gene operatively linked to said promoter, wherein the region in said DNA consisting of (i), (ii) and (iii) and DNA therebetween has a nucleotide sequence different from that of naturally occurring DNA, and said dominant activator sequence being characterized in that in naturally occurring DNA:

(I) it is associated with a naturally occurring gene that is expressed in a tissue-specific manner; and (II) it is locatable in naturally occurring DNA by association with a DNase I super hypersensitive site;

wherein said dominant activator sequence is characterized in that it stimulates expression of said structural gene when said DNA molecule is integrated into a genome of a host cell of said mammalian cell-type, such that said expression:

(a) is dependent on the number of copies of said gene that are integrated into said genome in that said expression increases as said number of copies of said gene increases; and (b) is independent of the integration site of said DNA molecule in said genome.

2. A DNA molecule according to claim 1, wherein said dominant activator sequence is a dominant activator sequence of the human β-globin locus.

3. A DNA molecule according to claim 2, wherein said dominant activator sequence is a dominant activator sequence of the 21 kb fragment of human genomic DNA extending from the ClaI site 1 kb 5' to the epsilon-globin gene in the β-globin locus to the BglII site 22 kb 5' to the epsilon-globin gene.

4. A DNA molecule according to claim 3, wherein said dominant activator sequence comprises one or more of the following fragments of said 21 kb fragment of human genomic DNA:

the 2.1 kb XbaI—XbaI fragment, the 1.5 kb KpnI-BglII fragment, and the 1.1 kb SacI—SacI fragment which comprises an internal SacI site.

5. A DNA molecule according to claim 1, wherein said dominant activator sequence is a dominant activator sequence of the human CD2 locus.

6. A DNA molecule according to claim 5, wherein said dominant activator sequence is within the 5.5 kb BamHI-XbaI fragment of human genomic DNA immediately 3' to the CD2 gene.

7. A mammalian host cell transformed with an isolated DNA molecule, comprising:

(i) a dominant activator sequence that is specific for a particular mammalian cell-type, (ii) a promoter that is functional in said particular mammalian cell-type, and (iii) a structural gene operatively linked to said promoter, wherein the region in said DNA consisting of (i), (ii) and (iii) and DNA therebetween has a nucleotide sequence different from that of naturally occurring DNA, and said dominant activator sequence being characterized in that in naturally occurring DNA:

(I) it is associated with a naturally occurring gene that is expressed in a tissue-specific manner; and (II) it is locatable in naturally occurring DNA by association with a DNase I super hypersensitive site;

wherein said dominant activator sequence is characterized in that it stimulates expression of said structural gene when said DNA molecule is integrated into a genome of a host cell of said mammalian cell-type, such that said expression:

(a) is dependent on the number of copies of said gene that are integrated into said genome in that said expression increases as said number of copies of said gene increases; and (b) is independent of the integration site of said DNA molecule in said genome.

8. A method of producing a polypeptide, comprising culturing a mammalian host cell transformed with an isolated DNA molecule, comprising:

a dominant activator sequence that is specific for a particular mammalian cell-type, (ii) a promoter that is functional in said particular mammalian cell-type, and (iii) a structural gene operatively linked to said promoter, wherein the region in said DNA consisting of (i), (ii) and (iii) and DNA therebetween has a nucleotide sequence different from that of naturally occurring DNA, and said dominant activator sequence being characterized in that in naturally occurring DNA:

(I) it is associated with a naturally occurring gene that is expressed in a tissue-specific manner; and (II) it is locatable in naturally occurring DNA by association with a DNase I super hypersensitive site;

wherein said dominant activator sequence is characterized in that it stimulates expression of said structural gene when said DNA molecule is integrated into a genome of a host cell of said mammalian cell-type, such that said expression:

(a) is dependent on the number of copies of said gene that are integrated into said genome in that said expression increases as said number of copies of said gene increases; and (b) is independent of the integration site of said DNA molecule in said genome.

9. A DNA molecule according to claim 1, said associated DNase I super hypersensitive site being subject to cleavage with DNase I in a time course incubation at 37° C. at a minimum concentration of about 5 µg/ml prior in time to cleavage of other DNase I-sensitive sites in and around said naturally occurring gene.

10. A DNA molecule according to claim 9, wherein said dominant activator sequence is locatable in naturally occurring DNA by association with a DNase I super hypersensitive site that is cleavable at a minimum concentration of DNase I of about 20 µg/ml.

11. A DNA molecule according to claim 10, wherein said dominant activator sequence is locatable in naturally occurring DNA by association with a DNase I super hypersensitive site that is cleavable at a minimum concentration of DNase I of about 60 µg/ml.

12. A DNA molecule according to claim 4, wherein said dominant activator sequence further comprises the 1.9 kb HindIII—HindIII fragment of said 21 kb fragment of human genomic DNA.

13. The mammalian host cell of claim 7, wherein said dominant activator sequence of said isolated DNA molecule is a dominant activator sequence of the human β-globin locus.

14. The mammalian host cell of claim 13, wherein said dominant activator sequence of the human β-globin locus is within the 21 kb fragment of human genomic DNA extending from the ClaI site 1 kb 5' to the epsilon-globin gene in the β-globin locus to the BglII site 22 kb 5' to the epsilon-globin gene.

15. The mammalian host cell of claim 14, wherein said dominant activator sequence of the human β-globin locus comprises one or more of the following fragments of said 21 kb fragment of human genomic DNA:

the 2.1 kb XbaI—XbaI fragment, the 1.5 kb XpnI-BglII fragment, and the 1.1 kb SacI—SacI fragment which comprises an internal SacI site.

16. The mammalian host cell of claim 7, wherein said dominant activator sequence of said isolated DNA molecule is a dominant activator sequence of the human CD2 locus.

17. The mammalian host cell of claim 16, wherein said dominant activator sequence of the human CD2 locus is within the 5.5 kb BamHI-XbaI fragment of human genomic DNA immediately 3' to the CD2 gene.

18. The mammalian host cell of claim 7, said associated DNase I super hypersensitive site of said dominant activator sequence being subject to cleavage with DNase I in a time course incubation at 37° C. at a minimum concentration of about 5 µg/ml prior in time to cleavage of other DNase I-sensitive sites in and around said naturally occurring gene.

19. The method of claim 8, wherein said dominant activator sequence of said isolated DNA molecule is a dominant activator sequence of the human β-globin locus.

20. The method of claim 19, wherein said dominant activator sequence of the human β-globin locus is within the 21 kb fragment of human genomic DNA extending from the ClaI site 1 kb 5' to the epsilon-globin gene in the β-globin locus to the BglII site 22 kb 5' to the epsilon-globin gene.

21. The method of claim 20, wherein said dominant activator sequence of the human β-globin locus comprises one or more of the following fragments of said 21 kb fragment of human genomic DNA:

the 2.1 kb XbaI—XbaI fragment, the 1.5 kb KpnI-BglII fragment, and the 1.1 kb SacI—SacI fragment which comprises an internal SacI site.

22. The method of claim 8, wherein said dominant activator sequence of said isolated DNA molecule is a dominant activator sequence of the human CD2 locus.

23. The method of claim 22, wherein said dominant activator sequence of the human CD2 locus is within the 5.5 kb BamHI-XbaI fragment of human genomic DNA immediately 3' to the CD2 gene.

24. The method of claim 8, said associated DNase I super hypersensitive site of said dominant activator sequence being subject to cleavage with DNase I in a time course incubation at 37° C. at a minimum concentration of about 5 µg/ml prior in time to cleavage of other DNase I-sensitive sites in and around said naturally occurring gene.

\* \* \* \* \*

UNITED STATES PATENT AND TRADEMARK OFFICE
CERTIFICATE OF CORRECTION

PATENT NO. : 5,532,143
DATED : Jul. 2, 1996
INVENTOR(S) : Franklin G. Grosveld and Dimitris Kioussis It is certified that error appears in the above-indentified patent and that said Letters Patent is hereby corrected as shown below:

On the Title Page
Under "Foreign Application Priority Data", insert --Aug. 8, 1988 PCT/GB88/00655--.

In col. 1, line 8, after "May 11, 1989", insert --, which was filed under 35 U.S.C. 371 as the national stage of PCT/GB88/00655, filed Aug. 8, 1988--.

Signed and Sealed this

Sixth Day of May, 1997

Attest:

BRUCE LEHMAN

*Attesting Officer*          *Commissioner of Patents and Trademarks*